(12) United States Patent
Meador et al.

(10) Patent No.: US 10,428,181 B2
(45) Date of Patent: Oct. 1, 2019

(54) POROUS CROSS-LINKED PARTIALLY ALIPHATIC POLYIMIDE NETWORKS

(71) Applicants: Ohio Aerospace Institute, Brook Park, OH (US); U.S. Government, represented by the Administrator of the National Aeronautics and Space Administration, Washington, DC (US)

(72) Inventors: Mary Ann B. Meador, Strongsville, OH (US); Baochau N. Nguyen, North Royalton, OH (US); Haiquan Guo, Avon, OH (US)

(73) Assignees: OHIO AEROSPACE INSTITUTE, Brook Park, OH (US); U.S. GOVERNMENT AS REPRESENTED BY THE ADMINISTRATOR OF THE NATIONAL AERONAUTICS AND SPACE ADMINISTRATION, Washington, DC (US)

( * ) Notice: Subject to any disclaimer, the term of this patent is extended or adjusted under 35 U.S.C. 154(b) by 65 days.

(21) Appl. No.: 15/729,941

(22) Filed: Oct. 11, 2017

(65) Prior Publication Data

US 2019/0106541 A1 Apr. 11, 2019

(51) Int. Cl.
*C08G 73/10* (2006.01)
*C08K 5/00* (2006.01)
(Continued)

(52) U.S. Cl.
CPC ............ *C08G 73/1007* (2013.01); *C08J 9/28* (2013.01); *C08K 5/0025* (2013.01); *C08K 5/095* (2013.01);
(Continued)

(58) Field of Classification Search
CPC ............... C08G 73/10; C08G 73/1007; C08G 73/1035; C08G 73/1039; C08G 73/1042;
(Continued)

(56) References Cited

U.S. PATENT DOCUMENTS 8,841,406 B2 9/2014 Meador
8,974,903 B2 3/2015 Meador
(Continued)

OTHER PUBLICATIONS

Garcia, et al., Synthesis and characterization of aliphatic-aromatic poly(ether amide)s, Macromol. Chem. Phys. 1997, vol. 198, pp. 727-737.
(Continued)

*Primary Examiner* — Shane Fang
(74) *Attorney, Agent, or Firm* — Pearne & Gordon LLP

(57) ABSTRACT

Porous cross-linked partially aliphatic polyimide networks are provided. The polyimide networks comprise a polyamic acid oligomer that (i) comprises a repeating unit of a dianhydride and a diamine and terminal functional groups, (ii) has an average degree of polymerization of 10 to 70, (iii) has been cross-linked via a cross-linking agent, comprising three or more cross-linking groups, at a balanced stoichiometry of the cross-linking groups to the terminal functional groups, and (iv) has been chemically imidized to yield the porous cross-linked polyimide network. The polyimide networks are partially aliphatic based on (a) the diamine comprising a first diamine and a second diamine, wherein the first diamine comprises a linear aliphatic backbone chain, and the second diamine does not, and/or (b) the dianhydride comprising a first dianhydride and a second dianhydride, wherein the first dianhydride comprises a linear aliphatic backbone chain, and the second dianhydride does not.

25 Claims, 14 Drawing Sheets
(7 of 14 Drawing Sheet(s) Filed in Color)

2,2-bis(4-[4-aminophenoxy]phenyl)propane
(BAPP)

3,3',4,4'-benzophenone tetracarboxylic dianhydride
(BTDA)

1,3,5-tris(4-aminophenoxy)benzene
(TAB)

4,4'-methylene-bis-diphenyldiisocyanate
(MDI)

1,4-diazobicyclo[2,2,2]octane
(DABCO)

Acetic anhydride
(AA)

Pyridine
(Py)

Triethylamine
(TEA)

(51) Int. Cl.
C08K 5/095 (2006.01)
C08J 9/28 (2006.01)
C08G 101/00 (2006.01)
C07C 63/68 (2006.01)

(52) U.S. Cl.
CPC ...... C07C 63/68 (2013.01); C08G 2101/0091 (2013.01); C08J 2379/08 (2013.01)

(58) Field of Classification Search
CPC .............. C08G 73/1046; C08G 73/105; C08G 73/1053; C08G 73/1057; C08G 73/106; C08G 73/1075
See application file for complete search history.

(56) References Cited

U.S. PATENT DOCUMENTS

| | | |
|---|---|---|
| 9,109,088 B2 | 8/2015 | Meador |
| 9,309,369 B1 | 4/2016 | Meador |
| 9,434,832 B1 | 9/2016 | Meador |

OTHER PUBLICATIONS

Shiotani, et al., Preparation of Polyimides Derived from Biphenyltetracarboxylic Dianhydrides and Aromatic Diamines Bearing Alkylene Spacers, Journal of Applied Polymer Science, 1999, vol. 74, pp. 2404-2413.

Balasubramanian, et al., Structure—property relationship of polyetherimide based on aromatic dianhydride and long alkyl chain containing aromatic diamines, High Performance Polymers, 2015, vol. 27(6), pp. 758-771.

Viggiano, et al., Effect of Bulky Substituents in the Polymer Backbone on the Properties of Polyimide Aerogels, ACS Applied Materials & Interfaces, 2017, vol. 9, pp. 8287-8296.

Guo, et al., Tailoring Properties of Cross-Linked Polyimide Aerogels for Better Moisture Resistance, Flexibility, and Strength, ACS Applied Materials & Interfaces, 2012, vol. 4, pp. 5422-5429.

Meador, et al., Polyimide Aerogels with Amide Cross-Links: A Low Cost Alternative for Mechanically Strong Polymer Aerogels, ACS Applied Materials & Interfaces, 2015, vol. 7, pp. 1240-1249

Meador, et al., Mechanically Strong, Flexible Polyimide Aerogels Cross-Linked with Aromatic Triamine, ACS Applied Materials & Interfaces, 2012, vol. 4, pp. 536-544.

Meador, et al., Effect of Branching on Rod-Coil Block Polyimides as Membrane Materials for Lithium Polymer Batteries, Chemistry of Materials, 2003, vol. 15, No. 15, pp. 3018-3025.

Meador, et al., Moisture-Resistant Polyimide Aerogels Containing Propylene Oxide Links in the Backbone, ACS Applied Materials & Interfaces, 2016, vol. 8, pp. 29073-29079.

Meador, et al., Use of Polyimide Aerogels as Lightweight, Multifunctional Materials for Aerospace Applications, Aug. 17, 2017, Presentation at ACS Meeting, Washington DC, United States.

Meador, Use of Polymer Aerogels as Lightweight, Multifunctional Materials for Aerospace Applications, Sep. 8, 2017, Presentation at Case Western Reserve University, Cleveland, Ohio, United States.

Pantoja et al., "Increased Flexibility in Polyimide Aerogels Using Aliphatic Spacers in the Polymer Backbone," ACS Appl. Mater. Interfaces, pp. 1-13, DOI: 10.1021/acsami.8b20420, available on line Feb. 22, 2019.

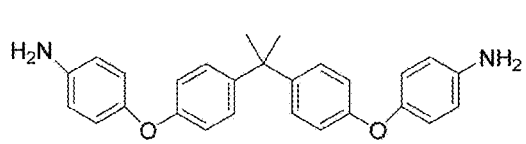
2,2-bis(4-[4-aminophenoxy]phenyl)propane
(BAPP)

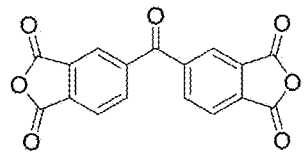
3,3',4,4'-benzophenone tetracarbocylic dianhydride
(BTDA)

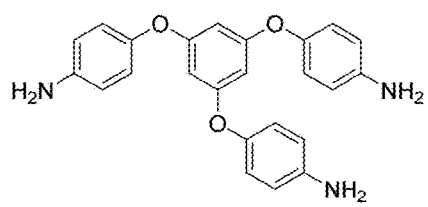
1,3,5-tris(4-aminophenoxy)benzene
(TAB)

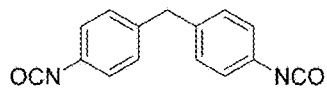
4,4'-methylene-bis-diphenyldiisocynate
(MDI)

1,4-diazobicyclo[2,2,2]octane
(DABCO)

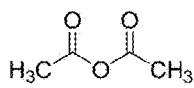
Acetic anhydride
(AA)

Pyridine
(Py)

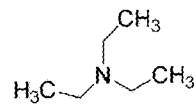
Triethylamine
(TEA)

FIG. 1

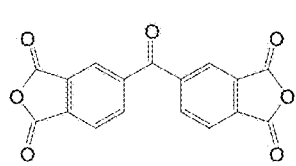
Benzophenone-3,3',4,4'-tetracarboxylic
dianhydride (BTDA)

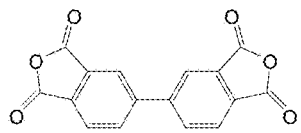
Biphenyl-3,3',4,4'-tetracarboxylic
dianhydride (BPDA)

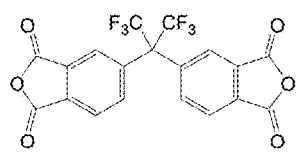
2,2'-Bis(3,4'-dicarboxyphenyl)hexafluoropropane)
dianhydride (HFDA)

FIG. 2

Desmodur Z4470 MPA/X
(IPDI trimer)

OAPS

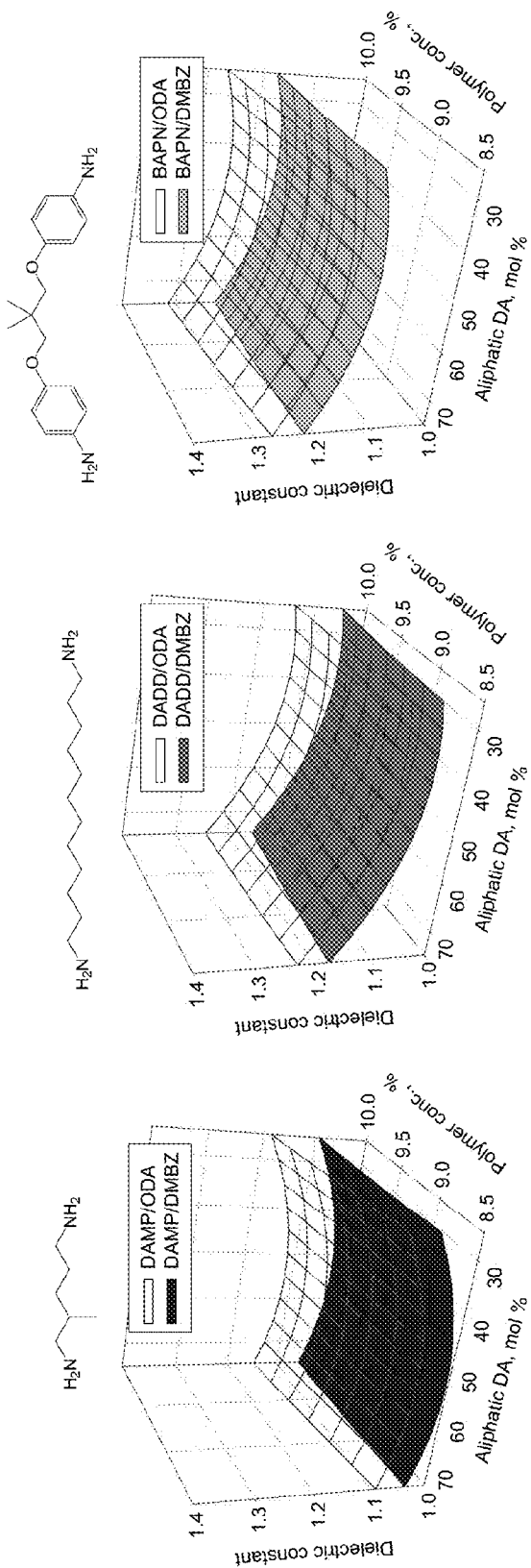
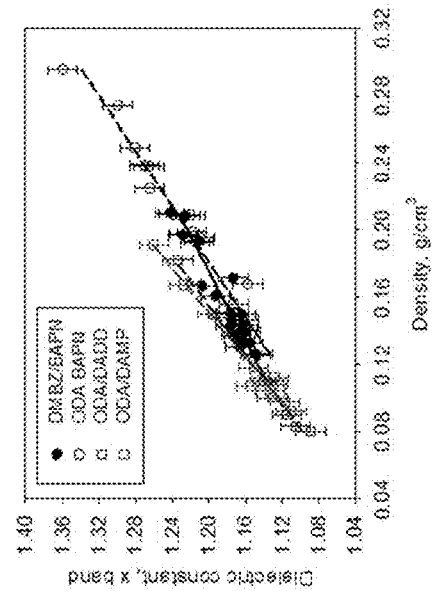
FIG. 14
FIG. 15

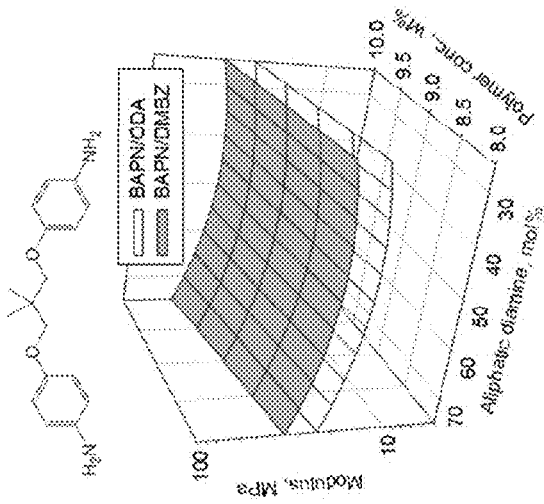
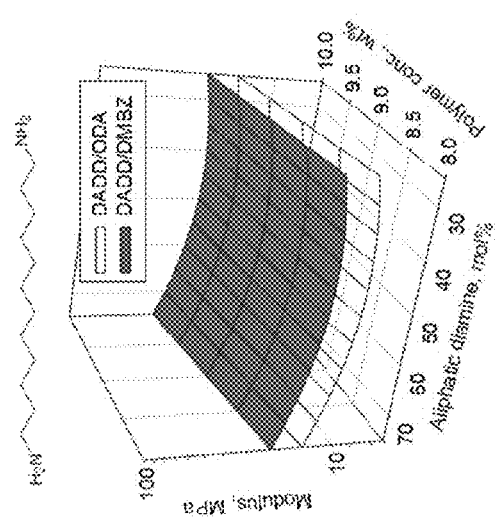
FIG. 16
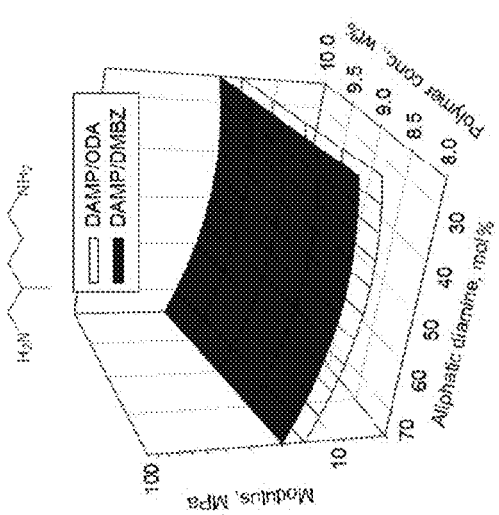
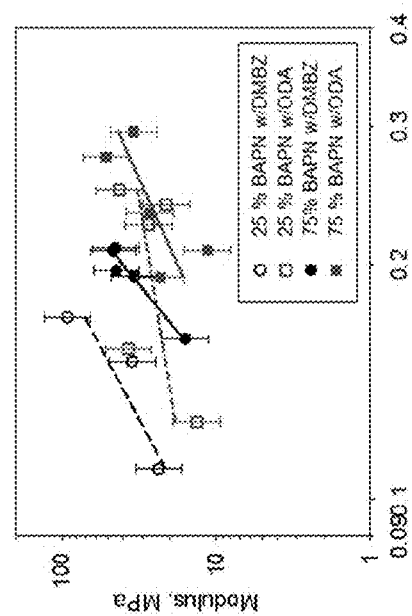
FIG. 17

US 10,428,181 B2

POROUS CROSS-LINKED PARTIALLY ALIPHATIC POLYIMIDE NETWORKS

STATEMENT OF GOVERNMENT-SPONSORED RESEARCH

This invention was made with government support under Contract No. NNC13BA01B awarded by NASA. The government has certain rights in this invention.

FIELD OF THE INVENTION

The present invention relates generally to porous cross-linked partially aliphatic polyimide networks, and more particularly to porous cross-linked partially aliphatic polyimide networks that comprise a polyamic acid oligomer comprising a repeating unit of a dianhydride and a diamine and terminal functional groups, wherein the polyimide network is partially aliphatic based on (a) the diamine comprising a first diamine and a second diamine, wherein the first diamine comprises a linear aliphatic backbone chain, and the second diamine does not, and/or (b) the dianhydride comprising a first dianhydride and a second dianhydride, wherein the first dianhydride comprises a linear aliphatic backbone chain, and the second dianhydride does not.

BACKGROUND OF THE INVENTION

Thermosetting polyimides are commercially available as uncured resins, stock shapes, thin sheets, laminates, and machines parts. Thermoplastic polyimides are very often called pseudothermoplastic. There are two general types of polyimides. One type, so-called linear polyimides, is made by combining imides into long chains. Aromatic heterocyclic polyimides are the other usual kind, where R' and R" are two carbon atoms of an aromatic ring. Examples of polyimide films include Apical, Kapton, UPILEX, VTEC PI, Norton TH and Kaptrex. Polyimides have been in mass production since 1955. Typical monomers include pyromellitic dianhydride and 4,4'-oxydianiline.

Lightweight, low density structures are desired for acoustic and thermal insulation for aerospace structures, habitats, and astronaut equipment and aeronautic applications. Aerogel is a manufactured material with the lowest bulk density of any known porous solid. It is derived from a gel in which the liquid component of the gel has been replaced with a gas. The result is an extremely low-density solid with several properties, most notably its effectiveness as a thermal insulator and its extremely low density. It is nicknamed frozen smoke, solid smoke, or blue smoke due to its translucent nature and the way light scatters in the material; however, it feels like expanded polystyrene to the touch. Aerogels are produced by extracting the liquid component of a gel through supercritical drying. This allows the liquid to be slowly drawn off without causing the solid matrix in the gel to collapse from capillary action, as would happen with conventional evaporation. The first aerogels were produced from silica gels.

Plain silica aerogels are brittle. Reinforcing the aerogel structure with polymer provides improvements in strength while maintaining low density and pore structure. Degradation of polymers used in cross-linking tends to limit use temperatures to below 150° C.

Polyimide aerogels can be fabricated from linear polyimides by allowing a low concentration polyimide/polyamic acid solution to gel, followed by heating to complete imidization and subsequent supercritical fluid extraction, as taught for example by Wendall, R., et al., WO/2004/009673, and Chidambareswarapattar, C., et. al., J. Mater. Chem. 2010, 20, 9666-9678. Polyimide aerogels prepared in this way from, for example, oxydianiline and pyrolimellitic dianhydride, have high surface areas, low density, low thermal conductivity, and good ductility. However, the gels shrink substantially, up to 40%, during supercritical fluid extraction.

Polyimide aerogels can also be synthesized by reaction of dianhydrides with di-isocyanates instead of diamines, as also reported by Chidambareswarapattar, C., et. al., J. Mater. Chem. 2010, 20, 9666-9678. This approach resulted in less shrinkage if gels were allowed to cure at room temperature, but results of thermogravimetric analyses of these aerogels revealed that imidization had not gone to completion.

Polyimide aerogels can also be synthesized by cross-linking anhydride end-capped polyamic acid oligomers via aromatic triamines, followed by thermal imidization, as taught for example by Kawagishi, K., et al., Macromol. Rapid Commun. 2007, 28, 96-100, and Meador, M. A. B., et al., Polym. Prepr. 2010, 51, 265-266. Unfortunately, the thermal imidization caused the gels to re-dissolve to some extent, suggesting hydrolysis of amic acid and disruption of the integrity of the polyimide aerogel network.

Polyimide aerogels also can be synthesized by cross-linking anhydride end-capped polyamic acid oligomers via aromatic triamines, followed by chemical imidization, as taught for example by Meador, et al. U.S. Pat. No. 9,109,088, or by cross-linking amine end-capped polyamic acid oligomers via triacid chlorides or polymaleic anhydrides, as taught by Meador, et al., ACS Appl. Mater. Interfaces 2015, 7, 1240-1249, and Guo, et al., RSC Adv. 2016, 6, 26055-26065. The properties of these polyimide aerogels are mainly dominated by the backbone chemistries of the oligomers, rather than the cross-linkers. For example, use of 3,3',4,4'-biphenyltetracarboxylic dianhydride ("BPDA") in combination with 2,2'-dimethylbenzidine ("DMBZ") in the oligomer backbone provides aerogels with a higher modulus at lower density due to the stiffness of the backbone, while 4,4'-oxydianiline ("ODA") used with BPDA in the backbone provides a lower modulus material that results in more flexible thin films. A combination of 50 mol % DMBZ and 50 mol % ODA used as diamine in a backbone with BPDA provides some moisture resistance and affords enough flexibility in the backbone to make foldable, thin films.

Moisture resistance is needed in the polyimide aerogels because the porous structures typically do not remain intact if wetted and re-dried, limiting technical applications to ones that will not result in wetting and re-drying. Thus, improvements in moisture resistance would be desirable. Also, although thin films made from these polyimide aerogels can be flexible, monolithic objects made from these polyimide aerogels having thickness of about 2 to 3 mm or greater are stiff, not flexible, and thus are not suitable for conformal applications. Thus, improvements in flexibility would be desirable too.

Accordingly, a need exists for improved porous cross-linked polyimide networks and methods of making such networks. A need also exists for porous cross-linked polyimide aerogels and thin films comprising porous cross-linked polyimide aerogels.

BRIEF SUMMARY OF THE INVENTION

A porous cross-linked partially aliphatic polyimide network is provided. The polyimide network comprises a polyamic acid oligomer that (i) comprises a repeating unit of a dianhydride and a diamine and terminal functional groups, (ii) has an average degree of polymerization of 10 to 70, (iii) has been cross-linked via a cross-linking agent, comprising three or more cross-linking groups, at a balanced stoichiometry of the cross-linking groups to the terminal functional groups, and (iv) has been chemically imidized to yield the porous cross-linked polyimide network.

The polyimide network is partially aliphatic based on one or both of the following:

(a) the diamine comprises: (i) a first diamine at 5 to 95% (mol %) and (ii) a second diamine at 5 to 95% (mol %), wherein (1) the first diamine comprises a first diamine linear aliphatic backbone chain comprising carbon atoms and optionally one or more oxygen atoms therein, extending a length of 3 to 30 atoms, and having a ratio of carbon:oxygen of 2:1 to 3:0, and (2) the second diamine does not comprise any linear aliphatic backbone chain extending a length of 3 or more atoms; or (b) the dianhydride comprises: (i) a first dianhydride at 5 to 95% (mol %) and (ii) a second dianhydride at 5 to 95% (mol %), wherein (1) the first dianhydride comprises a first dianhydride linear aliphatic backbone chain comprising carbon atoms and optionally one or more oxygen atoms therein, extending a length of 3 to 30 atoms, and having a ratio of carbon:oxygen of 2:1 to 3:0, and (2) the second dianhydride does not comprise any linear aliphatic backbone chain extending a length of 3 or more atoms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows chemical structures of various exemplary precursors and catalysts.

FIG. 2 shows chemical structures of exemplary dianhydrides.

FIG. 14 shows graphs of dielectric constant (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (SD=0.016, $R^2$=0.94).

FIG. 15 shows a graph of dielectric constant, x band (y-axis) as a function of polyimide aerogel density, $g/cm^3$ (x-axis), for DMBZ/BAPN (solid black circles), ODA/BAPN (open black circles), ODA/DADD (open blue squares), and ODA/DAMP (open red circles).

FIG. 16 shows graphs of modulus, MPa (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (SD=0.15, $R^2$=0.68).

FIG. 17 shows a graph of modulus, MPa (y-axis) as a function of polyimide aerogel density, $g/cm^3$ (x-axis), for 25% BAPN with DMBZ (open black circles), 25% BAPN with ODA (open red squares), 75% BAPN with DMBZ (solid black circles), and 75% BAPN with ODA (solid red squares).

DETAILED DESCRIPTION OF THE INVENTION

Figure 3:
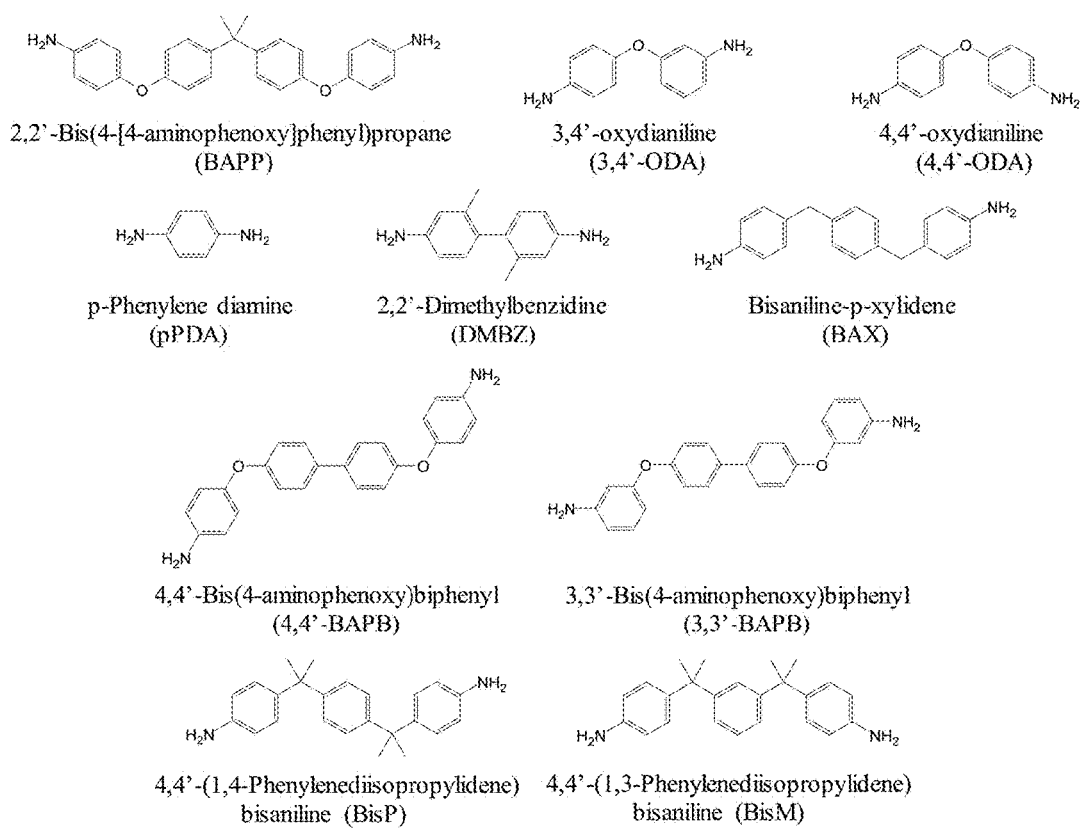
FIG. 3 shows chemical structures of exemplary diamines.

Described herein is a porous cross-linked partially aliphatic polyimide network. The polyimide network comprises a polyamic acid oligomer that (i) comprises a repeating unit of a dianhydride and a diamine and terminal functional groups, (ii) has an average degree of polymerization of 10 to 70, (iii) has been cross-linked via a cross-linking agent, comprising three or more cross-linking groups, at a balanced stoichiometry of the cross-linking groups to the terminal functional groups, and (iv) has been chemically imidized to yield the porous cross-linked polyimide network.

The polyimide network is partially aliphatic based on one or both of the following:

(a) the diamine comprises: (i) a first diamine at 5 to 95% (mol %) and (ii) a second diamine at 5 to 95% (mol %), wherein (1) the first diamine comprises a first diamine linear aliphatic backbone chain comprising carbon atoms and optionally one or more oxygen atoms therein, extending a length of 3 to 30 atoms, and having a ratio of carbon:oxygen of 2:1 to 3:0, and (2) the second diamine does not comprise any linear aliphatic backbone chain extending a length of 3 or more atoms; or (b) the dianhydride comprises: (i) a first dianhydride at 5 to 95% (mol %) and (ii) a second dianhydride at 5 to 95% (mol %), wherein (1) the first dianhydride comprises a first dianhydride linear aliphatic backbone chain comprising carbon atoms and optionally one or more oxygen atoms therein, extending a length of 3 to 30 atoms, and having a ratio of carbon:oxygen of 2:1 to 3:0, and (2) the second dianhydride does not comprise any linear aliphatic backbone chain extending a length of 3 or more atoms.

Surprisingly, it has been determined that the porous cross-linked partially aliphatic polyimide networks including diamine and/or dianhydride linear aliphatic backbone chains, and polyimide aerogels derived therefrom, can be made having increased moisture resistance and/or increased flexibility relative to polyimide networks not including the diamine and/or dianhydride linear aliphatic backbone chains, without sacrificing other desirable characteristics of polyimide networks, and polyimide aerogels derived therefrom, including low densities, high surface areas, and low dielectric constants.

Without wishing to be bound by theory, it is believed that use of a combination of diamines and/or dianhydrides including linear aliphatic backbone chains extending a length of 3 to 30 atoms, along with diamines and/or dianhydrides that do not include any linear aliphatic backbone chains, provides increased moisture resistance and/or increased flexibility while maintaining desirable properties. Using diamine and/or dianhydride linear aliphatic backbone chains comprising carbon atoms and optionally one or more oxygen atoms therein, extending a length of 3 to 30 atoms, and having a ratio of carbon:oxygen of 2:1 to 3:0 appears to provide sufficient flexibility within the polyimide backbone to allow corresponding materials to flex, without resulting in excessive shrinkage during drying, even for monolithic objects having thicknesses of 2 to 3 mm or greater. The resulting porous cross-linked partially aliphatic polyimide networks and polyimide aerogels may be used advantageously in conformal applications involving extreme temperatures and/or requiring low dielectric constants, for example as thermal insulation and/or antennas for aerospace applications.

Considering the porous cross-linked partially aliphatic polyimide network in more detail, as noted the porous cross-linked partially aliphatic polyimide network comprises a polyamic acid oligomer, and the polyamic acid oligomer comprises a repeating unit of a dianhydride and a diamine.

A variety of dianhydrides and diamines can be used, as shown in FIG. 1, FIG. 2, and FIG. 3. For example, the dianhydride can comprise one or more of biphenyl-3,3',4,4'-tetracarboxylic dianhydride ("BPDA"), benzophenone-3,3',4,4'-tetracarboxylic dianhydride ("BTDA"), pyromellitic dianhydride, 4,4'-oxydiphthalic anhydride, or 2,2'-bis(3,4'-dicarboxyphenyl)hexafluoropropane dianhydride ("HFDA"). Also for example, the diamine can comprise one or more of 2,2'-dimethylbenzidine ("DMBZ"), 2,2'-bis[4-(4-aminophenoxy)phenyl]propane ("BAPP"), 4,4'-diaminobenzophenone, 4,4'-oxydianiline ("4,4'-ODA" or "ODA"), 3,4'-oxydianiline ("3,4-ODA"), p-phenylene diamine ("PPDA"), bisaniline-p-xylidene ("BAX"), 4,4'-bis(4-aminophenoxy)biphenyl ("4,4'-BAPB"), 3,3'-bis(4-aminophenoxy)biphenyl ("3,3'-BAPB"), 4,4'-(1,4-phenylenediisopropylidene)bisaniline ("BisP"), or 4,4'-(1,3-phenylenediisopropylidene)bisaniline ("BisM"). Also for example, the second diamine can comprise a fluorinated diamine, such as 4,4'(hexafluoroisopropylidene)dianiline, 4,4'-(hexafluoroisopropylidene)bis(p-phenylenoxy)dianiline, or 2,2'-bis(trifluoromethyl)benzidine ("TFMB"). Additional suitable dianhydrides and diamines are discussed below.

The dianhydride and/or diamine can be selected based on being known to impart different properties to polyimides in general, and to cross-linked polyimide networks in particular, for example in order to tune cross-linked polyimide networks with respect to flexibility, hydrophobicity and wettability, and/or shrinkage. For example, BPDA, PPDA, and DMBZ are known to produce a rigid backbone in polyimide structures, whereas ODA and BTDA have flexible linking groups between phenyl rings resulting in less rigid structures, although, as discussed in Meador et al., U.S. Pat. No. 9,109,088, cross-linked polyimide networks can exhibit properties distinct from those of other polyimide structures in this regard. Also for example the dianhydride and/or diamine can be selected based on their hydrophobicity and contribution to wettability in order to make a corresponding cross-linked polyimide network moisture resistant. Also for example, various polyimide aerogels exhibit shrinkage when heated, with the extent of shrinkage depending on the diamine, e.g. with greatest shrinkage observed for DMBZ, and least shrinkage observed for 50% DMBZ/50% ODA, as reported by Meador et al., ACS Appl. Mater. Interfaces, 2015, 7:1240-1249. Also, shrinkage can be reduced when a bulky moiety is incorporated into the polyimide network, as reported by Viggiano et al., ACS Appl. Mater. Interfaces, 2017, 9:8287-8296.

Two or more dianhydrides and/or two or more diamines can also be used in combination, in this case specifically to make the polyimide network a partially aliphatic polyimide network, as discussed in detail below. For example, a diamine known to produce a rigid backbone in polyimide structures, such as PPDA or DMBZ, can be used in combination with a diamine having flexible linking groups between phenyl rings, such as ODA, to tailor properties of the resulting porous cross-linked polyimide network. Thus, for example, the diamine can comprise (i) ODA and (ii) PPDA or DMBZ. In accordance with this example, PPDA and ODA can be used in combination, such that the mole percent of PPDA can be varied from 0% to 100% of the total diamine, e.g. from 20% to 80%, 30% to 70%, 40% to 60%, or at about 50%, with the remaining diamine corresponding to ODA, e.g. from 80% to 20%, 70% to 30%, 60% to 40%, or at about 50%. Also in accordance with this example, DMBZ and ODA can be used in combination, such that the mole percent of DMBZ can be varied from 0% to 100% of the total diamine, e.g. from 20% to 80%, 30% to 70%, 40% to 60%, or at about 50%, with the remaining diamine corresponding to ODA, e.g. from 80% to 20%, 70% to 30%, 60% to 40%, or at about 50%. Additional combinations of diamines and/or combinations of dianhydrides are discussed below.

As noted, the polyamic acid oligomer also comprises terminal functional groups. A variety of terminal functional groups can be used. For example, the terminal functional groups can comprise (i) terminal anhydride groups, such that the polyamic acid oligomer comprises an anhydride end-capped polyamic acid oligomer, or (ii) terminal amine groups, such that the polyamic acid oligomer comprises an amine end-capped polyamic acid oligomer. Accordingly, in some examples the terminal functional groups comprise terminal anhydride groups. In accordance with these examples, the polyamic acid oligomer comprises an anhydride end-capped polyamic acid oligomer, i.e. both ends of the polyamic acid oligomer comprise a terminal anhydride group. Also in some examples the terminal functional groups comprise terminal amine groups. In accordance with these examples, the polyamic acid oligomer comprises an amine end-capped polyamic acid oligomer, i.e. both ends of the polyamic acid oligomer comprise a terminal amine group.

As noted, the polyamic acid oligomer has an average degree of polymerization of 10 to 70. For example, the average degree of polymerization can be 15 to 45, or 20 to 35.

As noted, the polyamic acid oligomer has been cross-linked via a cross-linking agent. By this it is meant that molecules of polyamic acid oligomer have been cross-linked to each other via the cross-linking agent.

Figure 4:
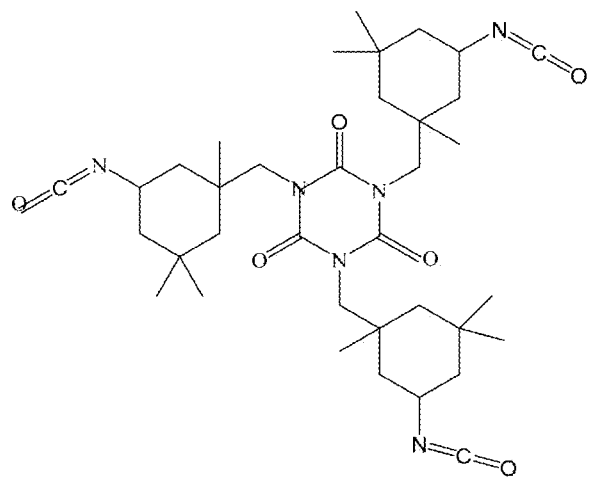
FIG. 4 shows a chemical structure of IPDI trimer.
Figure 5:
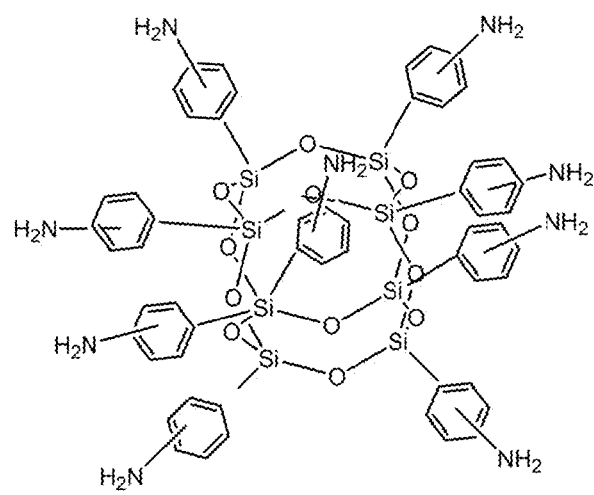
FIG. 5 shows a chemical structure of OAPS.

As noted, the cross-linking agent comprises three or more cross-linking groups. For example, the three or more cross-linking groups can comprise one or more of isocyanate groups, amine groups, anhydride groups, or acid chloride groups. Accordingly, in some examples the three or more cross-linking groups comprise isocyanate groups. In accordance with these examples, the cross-linking agent can comprise, for example, one or more of a triisocyanate, trifunctional aliphatic isocyanate Desmodur N3300A, or aliphatic polyisocyanate Desmodur Z4470 ("IPDI trimer"). IPDI trimer is shown in FIG. 4. Also in some examples the three or more cross-linking groups comprise amine groups. In accordance with these examples, the cross-linking agent can comprise, for example, one or more of a triamine, an aliphatic amine comprising three or more amines, an aliphatic triamine, an aromatic amine comprising three or more amine groups, an aromatic triamine, 1,3,5-tri(aminophenoxy)benzene, a silica cage structure decorated with three or more amines, octa(aminophenyl)silsesquioxane ("OAPS"), OAPS as a mixture of isomers having the ratio meta:ortho:para of 60:30:10, or para-OAPS. OAPS is shown in FIG. 5. Also in some examples the three or more cross-linking groups comprise anhydride groups. In accordance with these examples, the cross-linking agent can comprise, for example, one or more polymaleic anhydrides. Also in some examples the three or more cross-linking groups comprise acid chloride groups. In accordance with these examples, the cross-linking agent can comprise, for example, one or more of a triacid chloride or 1,3,5-benzenetricarbonyl trichloride.

Like the dianhydride and/or diamine, the cross-linking agent can be selected based on being known to impart different properties to polyimides in general, and to cross-linked polyimide networks in particular, for example in order to tune cross-linked polyimide networks with respect to flexibility, hydrophobicity and wettability, and/or shrinkage.

As noted, the cross-linking is carried out at a balanced stoichiometry of the cross-linking groups of the cross-linking agent to the terminal functional group of the polyamic acid oligomer. For example, for a cross-linking agent comprising three amine groups, such as 1,3,5-tri (aminophenoxy)benzene, the molar ratio of the cross-linking agent to the oligomer would be 2:3. Also for example, for a cross-linking agent comprising eight amine groups, such as octa(aminophenyl)silsesquioxane, the molar ratio of the cross-linking agent to the oligomer would be 1:4. As one of ordinary skill in the art will appreciate, carrying out the cross-linking at a balanced stoichiometry provides a cross-linked gel. This is in contrast to an imbalanced stoichiometry, which provides comb polymers that probably would not gel. Accordingly, as one of ordinary skill will also appreciate, a balanced stoichiometry need not be precisely balanced with respect to the molar ratio, but rather can tolerate some variation, e.g. plus or minus 10%, so long as the cross-linking provides a cross-linked gel.

As noted, the polyamic acid oligomer has been chemically imidized to yield the porous cross-linked partially aliphatic polyimide network. The chemical imidization can be carried out, for example, by use of an imidization catalyst. The imidization catalyst can comprise, for example, one or more of 1,4-diazabicyclo[2.2.2]-octane ("DABCO"), triethylamine, acetic anhydride, and pyridine, as shown in FIG. 1. The polyamic acid oligomer can be chemically imidized to completion, e.g. all of the amic acid groups of each repeating unit of the polyamic acid oligomer can have reacted, e.g. intra-molecularly, to yield imide units. The polyamic acid oligomer can also be chemically imidized without using thermal imidization, e.g. without using an increase in temperature during imidization in order to increase the rate of imidization. The polyamic acid oligomer can be chemically imidized in a homogenous solution of imidization catalyst and polyamic acid oligomer, e.g. based on mixing of the imidization catalyst into a solution including the polyamic acid oligomer and the cross-linking agent before phase separation occurs in the solution, i.e. before cross-linking of the polyamic acid oligomer occurs to a sufficient extent such that a gel of the cross-linked polyamic acid oligomer separates from the solution phase.

As noted, the polyimide network is partially aliphatic based on one or both of the following:

(a) the diamine comprises: (i) a first diamine at 5 to 95% (mol %) and (ii) a second diamine at 5 to 95% (mol %), wherein (1) the first diamine comprises a first diamine linear aliphatic backbone chain comprising carbon atoms and optionally one or more oxygen atoms therein, extending a length of 3 to 30 atoms, and having a ratio of carbon:oxygen of 2:1 to 3:0, and (2) the second diamine does not comprise any linear aliphatic backbone chain extending a length of 3 or more atoms; or (b) the dianhydride comprises: (i) a first dianhydride at 5 to 95% (mol %) and (ii) a second dianhydride at 5 to 95% (mol %), wherein (1) the first dianhydride comprises a first dianhydride linear aliphatic backbone chain comprising carbon atoms and optionally one or more oxygen atoms therein, extending a length of 3 to 30 atoms, and having a ratio of carbon:oxygen of 2:1 to 3:0, and (2) the second dianhydride does not comprise any linear aliphatic backbone chain extending a length of 3 or more atoms.

Figure 6:
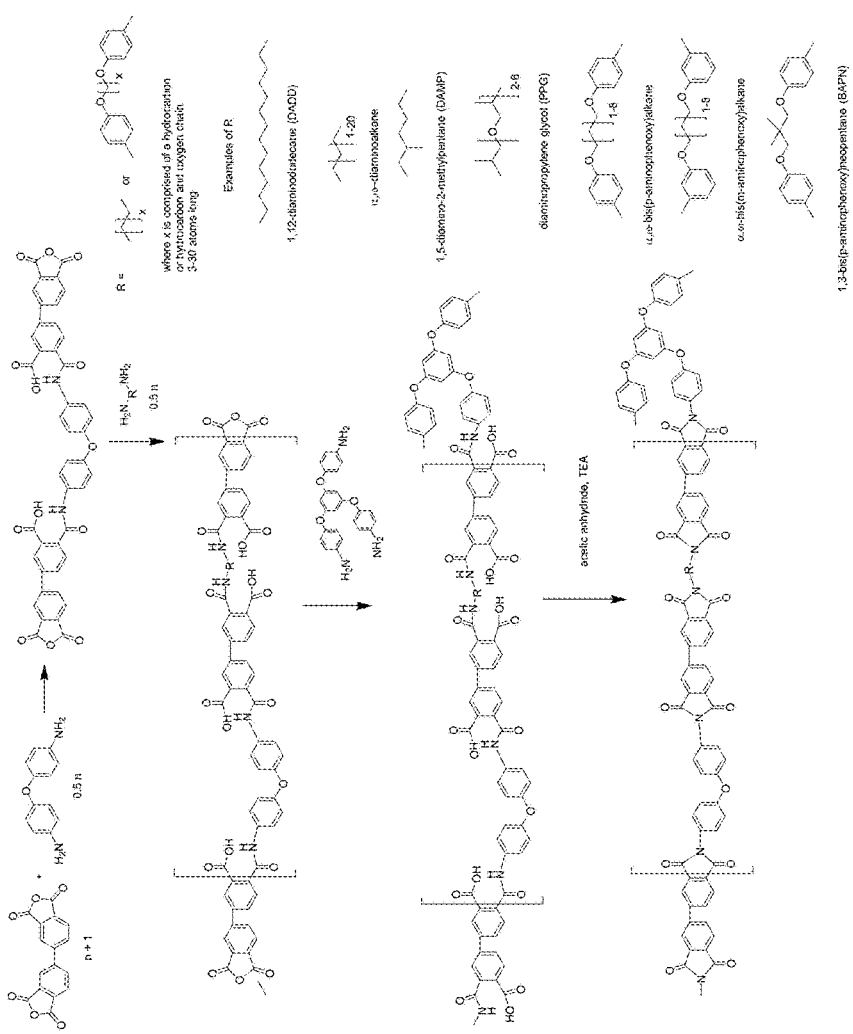
FIG. 6 shows an exemplary scheme for synthesis of a porous cross-linked partially aliphatic polyimide network and exemplary aliphatic diamines for use therein.

Thus, with reference to the scheme and exemplary diamines shown in FIG. 6, in some examples of the porous cross-linked partially aliphatic polyimide network the diamine comprises a first diamine at 5 to 95% (mol %) and a second diamine at 5 to 95% (mol %). In accordance with these examples, the first diamine comprises a first diamine linear aliphatic backbone chain. By this it is meant that the first diamine comprises an aliphatic moiety comprising a first chain end, a second chain end, and a contiguous linear sequence of atoms connected by covalent bonds extending between the first chain end and the second chain end, with the aliphatic moiety being positioned between a first amine group and a second amine group of the first diamine, such that the first chain end is connected within the first diamine proximal to the first amine group and distal to the second amine group, the second chain end is connected within the first diamine proximal to the second amine group and distal to the first amine group, and the contiguous linear sequence is not a component of a cyclic group within the first diamine. As will be appreciated, the first diamine linear aliphatic backbone chain is linear with respect to the first diamine based on having two ends and a chain extending therebetween and not being a component of a cyclic group within the first diamine. As also will be appreciated, the first diamine linear aliphatic backbone chain is a backbone chain with respect to the first diamine based on providing a linear connection between the two amine groups of the first diamine.

The first diamine linear aliphatic backbone chain comprises carbon atoms and optionally one or more oxygen atoms therein. The first diamine linear aliphatic backbone chain can comprise, for example, at least one of an alkyl chain, an unsubstituted alkyl chain, a substituted alkyl chain, an alkyl alkyl ether chain, an unsubstituted alkyl alkyl ether chain, or a substituted alkyl alkyl ether chain.

The first diamine linear aliphatic backbone chain extends a length of 3 to 30 atoms. By this it is meant that the first diamine linear aliphatic backbone chain includes a linear connection between the two amine groups of the first diamine, as discussed above, that is formed by 3 to 30 atoms, i.e. at least 3 atoms, and not more than 30 atoms, and more particularly that is formed by 3 to 30 atoms of carbon and, optionally, oxygen. The length of 3 to 30 atoms corresponds to atoms extending from the first chain end, to the second chain end, along the linear contiguous sequence of atoms therebetween, not for example to atoms of hydrogen or substituents that may be covalently bound to the 3 to 30 atoms that form the linear connection.

The first diamine linear aliphatic backbone chain has a ratio of carbon:oxygen of 2:1 to 3:0. In some examples, the first diamine linear aliphatic backbone chain has a ratio of carbon:oxygen of 2:1. In accordance with these examples, the linear connection can correspond to one or more alkyl ether chains. Also in some examples, the first diamine linear aliphatic backbone chain has a ratio of carbon:oxygen of 3:0. In accordance with these examples, the linear connection can correspond to an alkyl chain. Also in some examples, the first diamine linear aliphatic backbone chain has a ratio of carbon:oxygen that is between 2:1 and 3:0.

The first diamine thus includes a linear aliphatic backbone chain that can provide flexibility within the first diamine. Without wishing to be bound by theory, it is believed that the linear aliphatic backbone chain also can provide flexibility within a porous cross-linked partially aliphatic polyimide network comprising a polyamic acid oligomer that comprises a repeating unit of a dianhydride and a diamine, for which the diamine includes the first diamine.

In accordance with these examples, a variety of first diamines can be used. For example, the first diamine can comprise one or more of 1,3-bis(4-aminophenoxy)neopentane ("BAPN"), 1,4-bis(4-aminophenoxy)butane, 1,5-bis(4-aminophenoxy)pentane, 1,6-bis(4-aminophenoxy)hexane, 1,10-bis(4-aminophenoxy)decane, 1,3-diaminopropane, 1,4-diaminobutane, 1,6-diaminohexane, 1,7-diaminoheptane, 1,9-diaminononane, 1,10-diaminodecane, 1,12-diaminododecane ("DADD"), 1,5-diamino-2-methylpentane ("DAMP"), 2,2 dimethyl-1,3-propanediamine, bisaminopropyleneglycol, diaminopropylene glycol, α,ω-diaminoalkane, α,ω-bis(p-aminophenoxy)alkane, or α,ω-bis(m-aminophenoxy)alkane.

Also in accordance with these examples, the second diamine does not comprise any linear aliphatic backbone chain extending a length of 3 or more atoms. By this it is meant that the second diamine does not comprise any aliphatic moiety comprising a first chain end, a second chain end, and a contiguous linear sequence of atoms connected by covalent bonds extending between the first chain end and the second chain end, with the aliphatic moiety being positioned between a first amine group and a second amine group of the second diamine, such that the first chain end is connected within the second diamine proximal to the first amine group and distal to the second amine group, the second chain end is connected within the second diamine proximal to the second amine group and distal to the first amine group, for which the linear aliphatic backbone chain would include any linear connection between the two amine groups of the second diamine that would be formed by 3 or more atoms, and more particularly that would be formed by 3 or more atoms of carbon and, optionally, oxygen.

The second diamine thus does not include any linear aliphatic backbone chain that could provide flexibility within the second diamine. Without wishing to be bound by theory, it is believed that by not including any linear aliphatic backbone chain that could provide flexibility, that the second diamine promotes structural stability within a porous cross-linked partially aliphatic polyimide network comprising a polyamic acid oligomer that comprises a repeating unit of a dianhydride and a diamine, for which the diamine includes the second diamine.

In accordance with these examples, a variety of second diamines can be used. For example, the second diamine can comprise one or more of DMBZ, BAPP, 4,4'-diaminobenzophenone, 4,4'-ODA, 3,4-ODA, PPDA, BAX, 4,4'-BAPB, 3,3'-BAPB, BisP, BisM, 4,4'(hexafluoroisopropylidene)dianiline, 4,4'-(hexafluoroisopropylidene)bis(p-phenylenoxy)dianiline, or TFMB.

In accordance with these examples, a variety of dianhydrides can be used. For example, the dianhydride can comprise one or more of BPDA, BTDA, pyromellitic dianhydride, 4,4'-oxydiphthalic anhydride, or HFDA.

As noted above, in accordance with these examples the diamine comprises a first diamine at 5 to 95% (mol %) and a second diamine at 5 to 95% (mol %). In some examples the diamine comprises a first diamine at 20 to 80% (mol %) and a second diamine at 20 to 80% (mol %). Also in some examples the diamine comprises a first diamine at 25 to 75% (mol %) and a second diamine at 25 to 75% (mol %). Also in some examples the diamine comprises a first diamine at 35 to 65% (mol %) and a second diamine at 35 to 65% (mol %). Also in some examples the diamine comprises a first diamine at 45 to 55% (mol %) and a second diamine at 45 to 55% (mol %). Also in some examples the diamine comprises a first diamine at about 50% (mol %) and a second diamine at about 50% (mol %).

Figure 7:
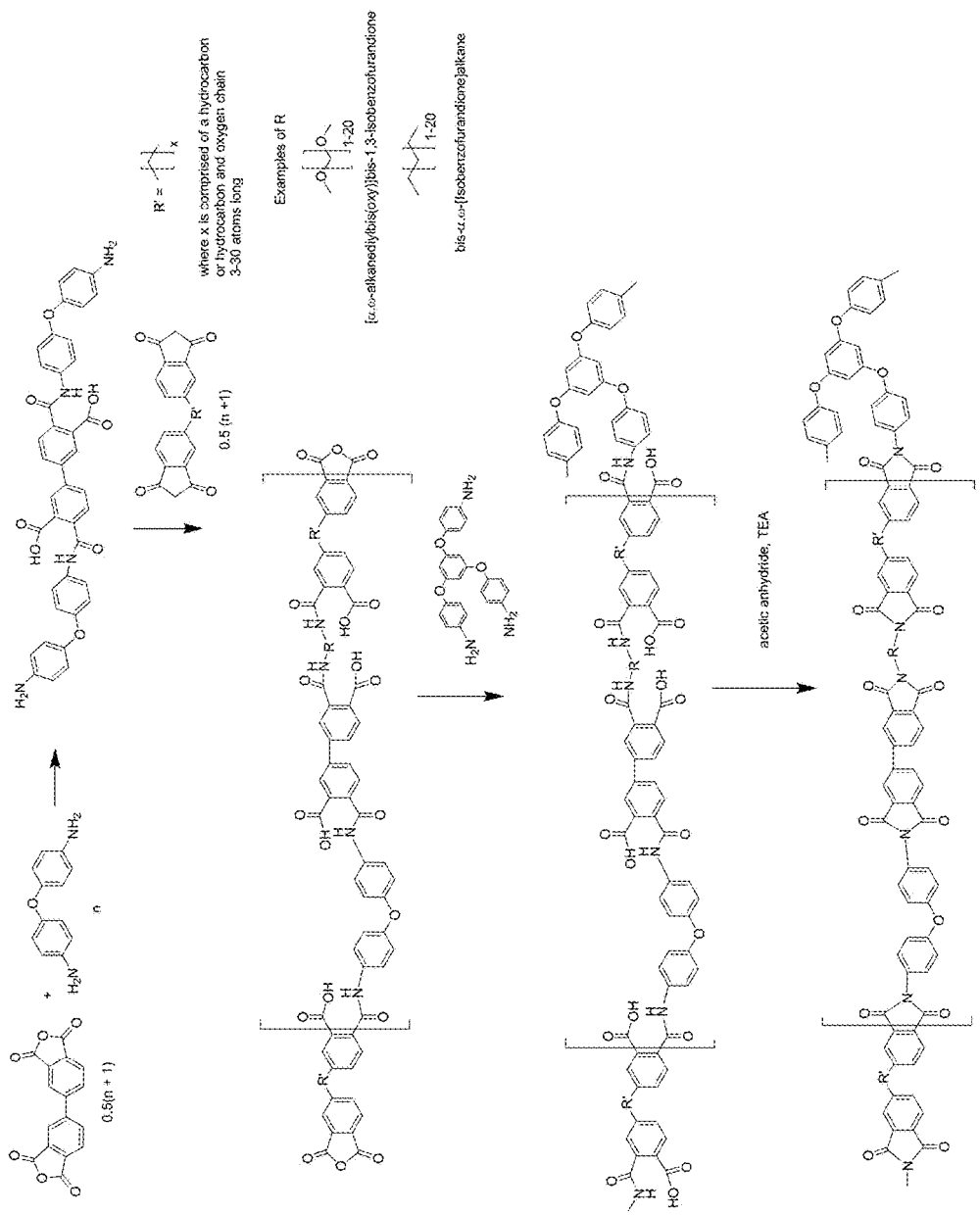
FIG. 7 shows an exemplary scheme for synthesis of a porous cross-linked partially aliphatic polyimide network and exemplary aliphatic dianhydrides for use therein.

Also, with reference to the scheme and exemplary dianhydrides shown in FIG. 7, in some examples of the porous cross-linked partially aliphatic polyimide network the dianhydride comprises a first dianhydride at 5 to 95% (mol %) and a second dianhydride at 5 to 95% (mol %). In accordance with these examples, the first dianhydride comprises a first dianhydride linear aliphatic backbone chain.

Similarly as for the first diamine, by this it is meant that the first dianhydride comprises an aliphatic moiety comprising a first chain end, a second chain end, and a contiguous linear sequence of atoms connected by covalent bonds extending between the first chain end and the second chain end, with the aliphatic moiety being positioned between a first anhydride group and a second anhydride group of the first dianhydride, such that the first chain end is connected within the first dianhydride proximal to the first anhydride group and distal to the second anhydride group, the second chain end is connected within the first dianhydride proximal to the second anhydride group and distal to the first anhydride group, and the contiguous linear sequence is not a component of a cyclic group within the first dianhydride. As will be appreciated, the first dianhydride linear aliphatic backbone chain is linear with respect to the first dianhydride based on having two ends and a chain extending therebetween and not being a component of a cyclic group within the first dianhydride. As will also be appreciated, the first dianhydride linear aliphatic backbone chain is a backbone chain with respect to the first dianhydride based on providing a linear connection between the two anhydride groups of the first dianhydride.

The first dianhydride linear aliphatic backbone chain comprises carbon atoms and optionally one or more oxygen atoms therein. The first dianhydride linear aliphatic backbone chain can comprise, for example, at least one of an alkyl chain, an unsubstituted alkyl chain, a substituted alkyl chain, an alkyl alkyl ether chain, an unsubstituted alkyl alkyl ether chain, or a substituted alkyl alkyl ether chain.

Similarly to the first diamine, the first dianhydride linear aliphatic backbone chain extends a length of 3 to 30 atoms. By this it is meant that the first dianhydride linear aliphatic backbone chain includes a linear connection between the two anhydride groups of the first dianhydride, as discussed above, that is formed by 3 to 30 atoms, i.e. at least 3 atoms, and not more than 30 atoms, and more particularly that is formed by 3 to 30 atoms of carbon and, optionally, oxygen. The length of 3 to 30 atoms corresponds to atoms extending from the first chain end, to the second chain end, along the linear contiguous sequence of atoms therebetween, not for example to atoms of hydrogen or substituents that may be covalently bound to the 3 to 30 atoms that form the linear connection.

The first dianhydride linear aliphatic backbone chain has a ratio of carbon:oxygen of 2:1 to 3:0. In some examples, the first dianhydride linear aliphatic backbone chain has a ratio of carbon:oxygen of 2:1. In accordance with these examples, the linear connection can correspond to one or more alkyl ether chains. Also in some examples, the first dianhydride linear aliphatic backbone chain has a ratio of carbon:oxygen of 3:0. In accordance with these examples, the linear connection can correspond to an alkyl chain. Also in some examples, the first dianhydride linear aliphatic backbone chain has a ratio of carbon:oxygen that is between 2:1 and 3:0.

The first dianhydride thus includes a linear aliphatic backbone chain that can provide flexibility within the first dianhydride. Without wishing to be bound by theory, it is believed that the linear aliphatic backbone chain also can provide flexibility within a porous cross-linked partially aliphatic polyimide network comprising a polyamic acid oligomer that comprises a repeating unit of a dianhydride and a diamine, for which the dianhydride includes the first dianhydride.

In accordance with these examples, a variety of first dianhydrides can be used. For example, the first dianhydrides can comprise one or more of [α,ω-alkanediylbis(oxy)]bis-1,3-isobenzofurandione or bis-α,ω-[isobenzofurandione]alkane.

Also in accordance with these examples, the second dianhydride does not comprise any linear aliphatic backbone chain extending a length of 3 or more atoms. By this it is meant that the second dianhydride does not comprise any aliphatic moiety comprising a first chain end, a second chain end, and a contiguous linear sequence of atoms connected by covalent bonds extending between the first chain end and the second chain end, with the aliphatic moiety being positioned between a first anhydride group and a second anhydride group of the second dianhydride, such that the first chain end is connected within the second dianhydride proximal to the first anhydride group and distal to the second anhydride group, the second chain end is connected within the second dianhydride proximal to the second anhydride group and distal to the first anhydride group, for which the linear aliphatic backbone chain would include any linear connection between the two anhydride groups of the second dianhydride that would be formed by 3 or more atoms, and more particularly that would be formed by 3 or more atoms of carbon and, optionally, oxygen.

The second dianhydride thus does not include any linear aliphatic backbone chain that could provide flexibility within the second dianhydride. Without wishing to be bound by theory, it is believed that by not including any linear aliphatic backbone chain that could provide flexibility, that the second dianhydride promotes structural stability within a porous cross-linked partially aliphatic polyimide network comprising a polyamic acid oligomer that comprises a repeating unit of a dianhydride and a diamine, for which the dianhydride includes the second dianhydride.

In accordance with these examples, a variety of second dianhydrides can be used. For example, the second dianhydride can comprise one or more of BPDA, BTDA, pyromellitic dianhydride, 4,4'-oxydiphthalic anhydride, or HFDA.

In accordance with these examples, a variety of diamines can be used. For example, the diamine can comprise one or more of DMBZ, BAPP, 4,4'-diaminobenzophenone, 4,4'-ODA, 3,4-ODA, PPDA, BAX, 4,4'-BAPB, 3,3'-BAPB, BisP, BisM, 4,4'(hexafluoroisopropylidene)dianiline, 4,4'-(hexafluoroisopropylidene)bis(p-phenylenoxy)dianiline, or TFMB.

As noted above, in accordance with these examples the dianhydride comprises a first dianhydride at 5 to 95% (mol %) and a second dianhydride at 5 to 95% (mol %). In some examples the dianhydride comprises a first dianhydride at 20 to 80% (mol %) and a second dianhydride at 20 to 80% (mol %). Also in some examples the dianhydride comprises a first dianhydride at 25 to 75% (mol %) and a second dianhydride at 25 to 75% (mol %). Also in some examples the dianhydride comprises a first dianhydride at 35 to 65% (mol %) and a second dianhydride at 35 to 65% (mol %). Also in some examples the dianhydride comprises a first dianhydride at 45 to 55% (mol %) and a second dianhydride at 45 to 55% (mol %). Also in some examples the dianhydride comprises a first dianhydride at about 50% (mol %) and a second dianhydride at about 50% (mol %).

Exemplary methods for making various porous cross-linked partially aliphatic polyimide network are provided in the examples that follow.

Also provided is an aerogel comprising the porous cross-linked partially aliphatic polyimide network. The aerogel can be obtained, for example, by supercritical fluid extraction, e.g. supercritical $CO_2$ extraction, of the porous cross-linked partially aliphatic polyimide network. The aerogel can have a low density, e.g. about 0.080 to 0.30 g/cm$^3$, 0.10 to 0.25 g/cm$^3$, 0.13 to 0.20 g/cm$^3$, or about 0.15 g/cm$^3$. The aerogel can have a high surface area, e.g. a BET surface area of 200 to 500 m$^2$/g, 230 to 430 m$^2$/g, or 260-400 m$^2$/g. The aerogel can have a water contact angle that provides for high moisture resistance, e.g. about 60 to 150°, 63 to 130°, 65 to 110°, or about 75°. The aerogel can have a low dielectric constant, e.g. about 1.08 to 1.36, 1.12 to 1.33, 1.15 to 1.30, or about 1.20. The aerogel can have a high Young's modulus, e.g. about 10 to 100 MPa, 10 to 80 MPa, 15 to 60 MPa, 20 to 50 MPa, or about 30 MPa. The aerogel can have a high porosity, e.g. about 78 to 95%, 80 to 93%, 83 to 92%, or about 88%. The aerogel can maintain flexibility at a thickness greater than that of a thin film, e.g. about 2 to 3 mm or greater.

An alternative porous cross-linked partially aliphatic polyimide network also is provided. The alternative polyimide network comprises a polyamic acid oligomer that (i) comprises a repeating unit of a dianhydride and a diamine and terminal functional groups, (ii) has an average degree of polymerization of 10 to 70, (iii) has been cross-linked via a cross-linking agent, comprising three or more cross-linking groups, at a balanced stoichiometry of the cross-linking groups to the terminal functional groups, and (iv) has been chemically imidized to yield the alternative porous cross-linked polyimide network.

The alternative polyimide network is partially aliphatic based on the following: the diamine comprises: (i) a cyclic aliphatic diamine at 5 to 95% (mol %) and (ii) a second diamine at 5 to 95% (mol %), wherein (1) the cyclic aliphatic diamine comprises an aliphatic ring structure, (2) the second diamine does not comprise any linear aliphatic backbone chain extending a length of 3 or more atoms, and (3) the cyclic aliphatic diamine and the second diamine are not the same.

The alternative porous cross-linked partially aliphatic polyimide network can be made similarly as for the polyimide network described above, except that a cyclic aliphatic diamine comprising an aliphatic ring structure, such as a cyclohexane structure, is incorporated instead of the first diamine as described above. Suitable cyclic aliphatic diamines comprising an aliphatic ring structure, such as a cyclohexane structure, include, for example, 1,3-diaminocyclohexane, 1,4 diaminocyclohexane, 1,3-cyclohexanebis (methylamine), or 4,4'methylenebis(cyclohexylamine). Additional suitable cyclic aliphatic diamines can comprise, for example, a cycloheptane structure, a cyclooctane structure, and/or a cyclononane structure, e.g. 1,4-diaminocycloheptane, 1,4-diaminocyclooctane, and/or 1,4-diaminocyclononane, respectively, among others.

Also provided is an alternative aerogel comprising the alternative porous cross-linked partially aliphatic polyimide network. The alternative aerogel can be made similarly as the aerogel described above. The alternative aerogel can have properties as described for the aerogel described above.

EXAMPLES

Initial Example

Initial attempts to prepare porous cross-linked partially aliphatic polyimide networks including long chain polyethylene/polypropylene oxide diamines (JEFFAMINES), for purposes of making polyimide aerogels with increased moisture resistance and/or flexibility, resulted in excessive shrinkage of the polyimide networks upon supercritical drying.

Figure 8:
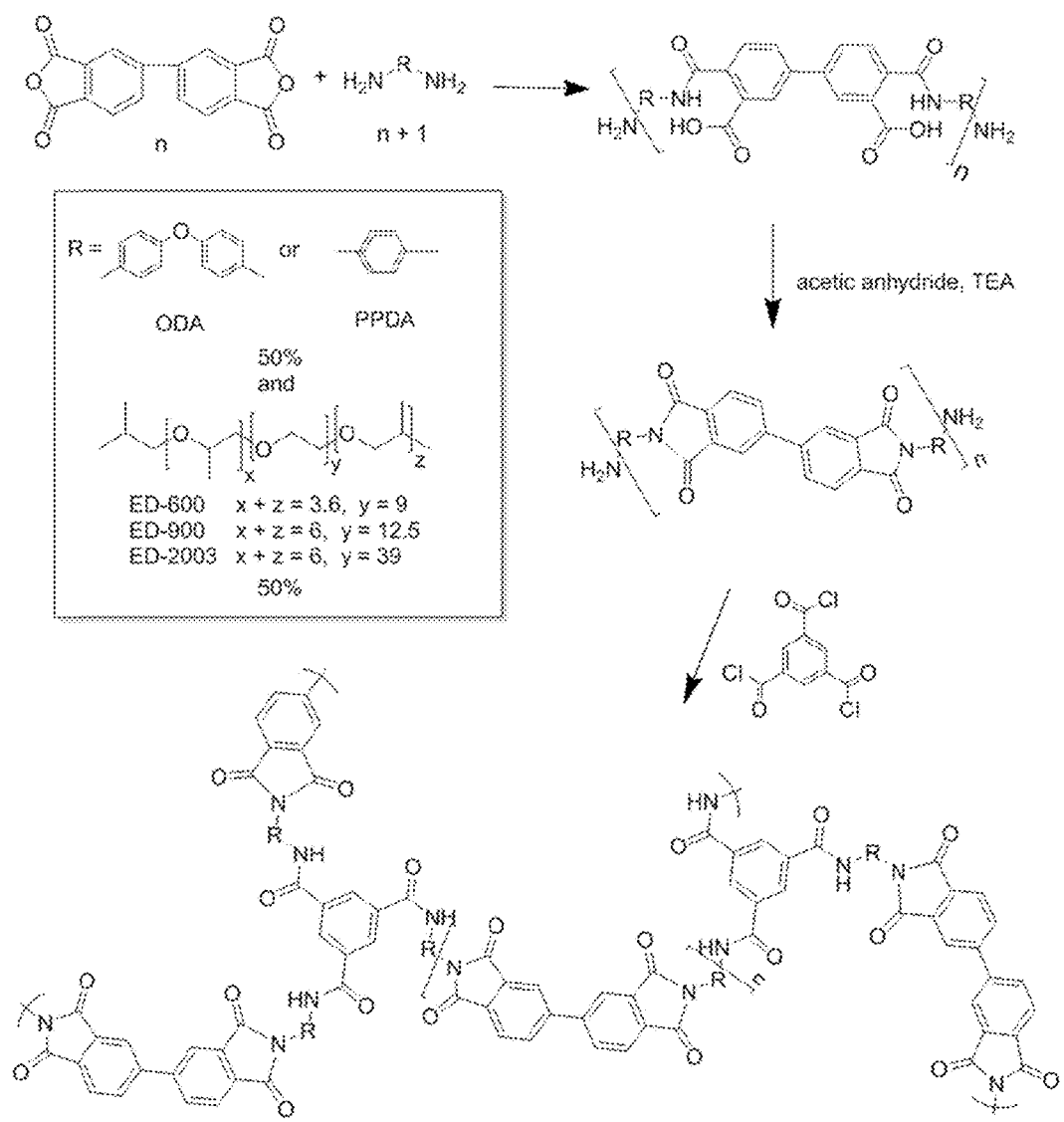
FIG. 8 shows a scheme for synthesis of initial polyimide networks, corresponding to gels, made using a combination of 50% aromatic diamine with 50% long chain polyethylene/polypropylene oxide diamines.

Specifically, initial polyimide networks, corresponding to gels, were made using a combination of 50% aromatic diamine with 50% long chain polyethylene/polypropylene oxide diamines according to the scheme as shown in FIG. 8. All such initial polyimide networks that were tested exhibited high shrinkage (54-75%) upon supercritical drying. Results are shown in TABLE 1. Bulk densities ranged from 0.5 to 1.3 g/cm$^3$, whereas desirable densities for aerogels are typically in the range of 0.05 to 0.3 g/cm$^3$.

TABLE 1

Formulations and properties of porous cross-linked partially aliphatic polyimide network, including JEFFAMINES, and polyimide aerogels derived therefrom.

| Sample | Polymer conc., wt % | n | JEFFAMINE | Aromatic Diamine | Shrinkage, % | Bulk density, g/cm$^3$ |
|---|---|---|---|---|---|---|
| 1 | 10 | 20 | ED600 | ODA | 54.26 | 0.5685 |
| 2 | 10 | 10 | ED600 | ODA | 58.05 | 0.6775 |
| 3 | 10 | 20 | ED900 | ODA | 62.55 | 1.2179 |
| 4 | 10 | 10 | ED900 | ODA | 64.50 | 1.1913 |
| 5 | 10 | 20 | ED2003 | ODA | 68.16 | 1.1868 |
| 6 | 7 | 12.5 | ED900 | ODA | 63.30 | 1.2227 |
| 7 | 8.5 | 20 | ED900 | ODA | 62.32 | 1.2288 |
| 8 | 10 | 20 | ED2003 | ODA | 66.85 | 1.2279 |
| 9 | 7 | 12.5 | ED600 | PPDA | 62.47 | 1.1984 |
| 10 | 10 | 12.5 | ED600 | ODA | 58.37 | 0.7929 |
| 11 | 10 | 12.5 | ED600 | PPDA | 57.71 | 0.7595 |
| 12 | 10 | 40 | ED600 | ODA | 57.87 | 0.9359 |
| 13 | 10 | 40 | ED600 | PPDA | 61.81 | 1.2296 |
| 14 | 10 | 40 | ED600 | PPDA | 62.28 | 1.2817 |
| 15 | 10 | 10 | ED2003 | ODA | 70.29 | 1.1768 |

These results suggested that it would not be possible to increase moisture resistance and/or flexibility of porous cross-linked polyimide networks and polyimide aerogels to any substantial degree without substantially compromising desirable properties of the polyimide aerogels.

Example 1

Surprisingly it has been determined that porous cross-linked partially aliphatic polyimide networks including diamine and/or dianhydride linear aliphatic backbone chains extending a length of 3 to 30 atoms, and polyimide aerogels derived therefrom, can be made having increased moisture resistance and/or increased flexibility relative to polyimide networks not including the diamine and/or dianhydride linear aliphatic backbone chains, without sacrificing other desirable characteristics of polyimide networks, and polyimide aerogels derived therefrom, including low densities, high surface areas, and low dielectric constants.

Specifically, use of a combination of the diamine and/or dianhydride linear aliphatic backbone chains, along with diamines and/or dianhydrides that do not include any linear aliphatic backbone chains, provides increased moisture resistance and/or increased flexibility while maintaining structural integrity. Using diamine and/or dianhydride linear aliphatic backbone chains comprising carbon atoms and optionally one or more oxygen atoms therein, extending a length of 3 to 30 atoms, and having a ratio of carbon:oxygen of 2:1 to 3:0 appears to provide sufficient flexibility within the polyimide backbone to allow corresponding materials to flex, without resulting in excessive shrinkage during drying.

In a first example, poly(amic acid) oligomer was formulated in NMP using a molar ratio of BPDA to total diamines of (n+1) to n, which is formulated to provide oligomers with an average of n repeat units terminated with anhydride. The mole percent of diamine DADD in place of ODA ranges from 0 to 75 mol %. TAB was used to react with the terminal anhydride groups on the poly(amic acid) oligomers. The total weight of precursors in solution was formulated to be 8.5 to 11.5 w/w %. A TAB cross-linked sample procedure for an oligomer (n=30) made using 75 mol % DADD and 25 mol % ODA, total precursor weight is 8.5 w/w % is as follows: 50 ml NMP was used to dissolve DADD (2.0119 g, 10.05 mmol) at 65° C. While stirring, BPDA (4.0732 g, 13.84 mmol) was added in DADD solution at 65° C. After it was fully reacted, ODA (0.6707 g, 3.35 mmol) in 10 mL NMP was further added. When the mixture cools down, a solution of TAB (0.1189 g, 0.3 mmol) in 6.756 mL NMP followed by acetic anhydride (10.469 ml, 110.75 mmol) and then TEA (3.86 mL, 27.69 mmol) were added. Acetic anhydride to BPDA is formulated in the ratios 8:1. The ratio of TEA to BPDA is 2:1. The solution was continually stirred for 10 minutes and then poured into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. The gels which formed within 30 minutes were aged in the mold for one day before extracting into 75% NMP in acetone. The solvent within the gels was then gradually exchanged to acetone in 24 hour intervals starting with 75% NMP in acetone, followed by 25% NMP in acetone and finally three more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 75° C. overnight. The dry polyimide aerogels produced in this way have a density of 0.098 g/cm$^3$.

Example 2

In another example, poly(amic acid) oligomer was formulated in NMP using a molar ratio of BPDA to total diamines of (n+1) to n, which is formulated to provide oligomers with an average of n repeat units terminated with anhydride. The mole percent of diamine DAMP in place of ODA ranges from 0 to 75 mol %. TAB was used to react with the terminal anhydride groups on the poly(amic acid) oligomers. The total weight of precursors in solution was formulated to be 8.5 to 11.5 w/w %. A TAB cross-linked sample procedure for an oligomer (n=30) made using 75 mol % DAMP and 25 mol % ODA, total precursor weight is 11.5 w/w % is as follows: 50 ml NMP was used to dissolve DAMP (2.117 ml, 15.67 mmol) at 65° C. While stirring, BPDA (6.3522 g, 21.59 mmol) was added in DAMP solution at 65° C. After it was fully reacted, ODA (1.0459 g, 5.22 mmol) in 10 mL NMP was further added. When the mixture cools down, a solution of TAB (0.1855 g, 0.46 mmol) in 5.661 mL NMP followed by acetic anhydride (16.327 ml, 172.72 mmol) and then TEA (6.018 mL, 43.18 mmol) were added. Acetic anhydride to BPDA is formulated in the ratios 8:1. The ratio of TEA to BPDA is 2:1. The solution was continually stirred for 10 minutes and then poured into a mold and let it gel. The gels were aged, extracted, washed and dried as described in example 1. The dry polyimide aerogels produced in this way have a density of 0.15 g/cm$^3$.

Example 3

In another example, poly(amic acid) oligomer was formulated in NMP using a molar ratio of BPDA to total diamines of (n+1) to n, which is formulated to provide oligomers with an average of n repeat units terminated with anhydride. The mole percent of diamine DADD in place of DMBZ ranges from 0 to 75 mol %. TAB was used to react with the terminal anhydride groups on the poly(amic acid) oligomers. The total weight of precursors in solution was formulated to be 8 to 11.5 w/w %. A TAB cross-linked sample procedure for an oligomer (n=30) made using 75 mol % DADD and 25 mol % DMBZ, total precursor weight is 8 w/w % is as follows: 40 ml NMP was used to dissolve DADD (1.8817 g, 9.4 mmol) at 65° C. While stirring, BPDA (3.8095 g, 12.95 mmol) was added in DADD solution at 65° C. After it was fully reacted, DMBZ (0.6650 g, 3.13 mmol) in 20 mL NMP was further added. When the mixture cools down, a solution of TAB (0.1112 g, 0.28 mmol) in 7.121 mL NMP followed by acetic anhydride (9.791 ml, 103.58 mmol) and then TEA (3.609 mL, 25.90 mmol) were added. Acetic anhydride to BPDA is formulated in the ratios 8:1. The ratio of TEA to BPDA is 2:1. The solution was continually stirred for 10 minutes and then poured into a mold and let it gel. The gels were aged, extracted, washed and dried as described in example 1. The dry polyimide aerogels produced in this way have a density of 0.09 g/cm$^3$.

Example 4

In another example, poly(amic acid) oligomer was formulated in NMP using a molar ratio of BPDA to total diamines of (n+1) to n, which is formulated to provide oligomers with an average of n repeat units terminated with anhydride. The mole percent of diamine DAMP in place of DMBZ ranges from 0 to 75 mol %. TAB was used to react with the terminal anhydride groups on the poly(amic acid) oligomers. The total weight of precursors in solution was formulated to be 8 to 11.5 w/w %. A TAB cross-linked sample procedure for an oligomer (n=30) made using 75 mol % DAMP and 25 mol % DMBZ, total precursor weight is 8 w/w % is as follows: 40 ml NMP was used to dissolve DAMP (1.462 ml, 10.82 mmol) at 65° C. While stirring, BPDA (4.3868 g, 14.91 mmol) was added in DAMP solution at 65° C. After it was fully reacted, DMBZ (0.7658 g, 3.61 mmol) in 20 mL NMP was further added. When the mixture cools down, a solution of TAB (0.1281 g, 0.32 mmol) in 7.121 mL NMP followed by acetic anhydride (11.275 ml, 119.28 mmol) and then TEA (4.156 mL, 29.82 mmol) were added. Acetic anhydride to BPDA is formulated in the ratios 8:1. The ratio of TEA to BPDA is 2:1. The solution was continually stirred for 10 minutes and then poured into a mold and let it gel. The gels were aged, extracted, washed and dried as described in example 1. The dry polyimide aerogels produced in this way have a density of 0.10 g/cm$^3$.

Example 5

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of DMBZ ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=30) made using 75 mol % BAPN and 25 mol % DMBZ, total precursor weight is 7 w/w % is as follows: To the solution of DMBZ (0.3403 g, 1.60 mmol), in 42 ml NMP, was added BPDA (1.9494 g, 6.63 mmol). The mixture was stirred until a homogeneous solution was obtained. BAPN (1.3771 g, 4.81 mmol) was then introduced. Once the solution was well mixed, the cross-linker TAB (0.0719 g, 0.142 mmol), dissolved in 3.25 ml NMP, was dispensed into the poly(amic acid) solution, followed by acetic anhydride (5.00 ml, 53.04 mmol) and triethyl amine (1.85 ml, 13.26 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 40 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.1608 g/cm$^3$.

Example 6

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of DMBZ ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=45) made using 50 mol % BAPN and 50 mol % DMBZ, total precursor weight is 8.5 w/w % is as follows: To the solution of DMBZ (0.8663 g, 4.08 mmol), in 41 ml NMP, was added BPDA (2.4546 g, 8.34 mmol). The mixture was stirred until a homogeneous solution was obtained. BAPN (1.1686 g, 4.08 mmol) was then introduced. Once the solution was well mixed, the cross-linker TAB (0.0610 g, 0.121 mmol), dissolved in 3.50 ml NMP, was dispensed into the poly(amic acid) solution, followed by acetic anhydride (6.31 ml, 66.72 mmol) and triethyl amine (2.35 ml, 16.68 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 30 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.1409 g/cm$^3$.

Example 7

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of DMBZ ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=60) made using 25 mol % BAPN and 75 mol % DMBZ, total precursor weight is 10 w/w % is as follows: To the solution of DMBZ (1.5957 g, 7.52 mmol), in 40 ml NMP, was added BPDA (2.9977 g, 10.20 mmol). The mixture was stirred until a homogeneous solution was obtained. BAPN (0.7175 g, 2.51 mmol) was then introduced. Once the solution was well mixed, the cross-linker TAB (0.0562 g, 0.111 mmol), dissolved in 3.75 ml NMP, was dispensed into the poly(amic acid) solution, followed by acetic anhydride (7.70 ml, 81.60 mmol) and triethyl amine (2.85 ml, 20.40 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 25 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.1667 g/cm$^3$.

Example 8

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of ODA ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=30) made using 75 mol % BAPN and 25 mol % ODA, total precursor weight is 7 w/w % is as follows: To the solution of ODA (0.3228 g, 1.61 mmol), in 42 ml NMP, was added BPDA (1.9602 g, 6.66 mmol). The mixture was stirred until a homogeneous solution was obtained. BAPN (1.3848 g, 4.84 mmol) was then introduced. Once the solution was well mixed, the cross-linker TAB (0.0723 g, 0.143 mmol), dissolved in 3.25 ml NMP, was dispensed into the poly(amic acid) solution, followed by acetic anhydride (5.05 ml, 53.28 mmol) and triethyl amine (1.85 ml, 13.32 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 40 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.1924 $g/cm^3$.

Example 9

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of DMBZ ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=45) made using 50 mol % BAPN and 50 mol % DMBZ, total precursor weight is 8.5 w/w % is as follows: To the solution of ODA (0.8267 g, 4.13 mmol), in 41 ml NMP, was added BPDA (2.4834 g, 8.44 mmol). The mixture was stirred until a homogeneous solution was obtained. BAPN (1.1823 g, 4.13 mmol) was then introduced. Once the solution was well mixed, the cross-linker TAB (0.0617 g, 0.122 mmol), dissolved in 3.50 ml NMP, was dispensed into the poly(amic acid) solution, followed by acetic anhydride (6.40 ml, 66.52 mmol) and triethyl amine (2.35 ml, 16.88 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 30 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.2090 $g/cm^3$.

Example 10

In another example, poly(amic acid) oligomer was formulated in NMP using a molar ratio of total diamines to BPDA of n to (n+1), which is formulated to provide oligomers with an average of n repeat units terminated with anhydride. The mole percent of diamine BAPN in place of DMBZ ranges from 0 to 75 mol %. TAB was used to react with the terminal anhydride groups on the poly(amic acid) oligomers. The total weight of precursors in solution was formulated to be 7 to 10 w/w %. A TAB cross-linked sample procedure for an oligomer (n=60) made using 25 mol % BAPN and 75 mol % DMBZ, total precursor weight is 10 w/w % is as follows: To the solution of ODA (1.5328 g, 7.66 mmol), in 40 ml NMP, was added BPDA (3.0531 g, 10.40 mmol). The mixture was stirred until a homogeneous solution was obtained. BAPN (0.7307 g, 2.55 mmol) was then introduced. Once the solution was well mixed, the cross-linker TAB (0.0572 g, 0.113 mmol), dissolved in 3.75 ml NMP, was dispensed into the poly(amic acid) solution, followed by acetic anhydride (7.85 ml, 83.20 mmol) and triethyl amine (2.90 ml, 20.80 mmol) was added. Acetic anhydride to BPDA is formulated in the ratios 8:1. The ratio of TEA to BPDA is 2:1. The solution was into a mold. The mold shape and size can be varied determined by the need. One kind of mold is a 20 mL syringe mold (2 cm in diameter), prepared by cutting off the needle end of the syringe and extending the plunger all the way out. One kind of mold is silicone mold with opening on top with different sizes. Another kind of mold is a thin block, closed mold made of two aluminum plate with a 2 mm spacer. The gels which formed within 25 minutes were aged in the mold for one day before extracting into 50% NMP in acetone. The solvent within the gels was then gradually exchanged to acetone in 24 hour intervals starting with 50% NMP in acetone, followed five more times with 100% acetone. The gels were then placed in a supercritical fluid extraction chamber in acetone, and washed with liquid $CO_2$ then the $CO_2$ was converted into a supercritical state and gaseous $CO_2$ was slowly vented out. The resulted aerogel was further vacuum dried at 80° C. overnight. The dry polyimide aerogels produced in this way have a density of 0.2245 $g/cm^3$.

Example 11

Porous cross-linked partially aliphatic polyimide networks and polyimide aerogels were prepared as described in the previous examples. Properties of the polyimide networks and polyimide aerogels, such as density, shrinkage, porosity, surface area, Young's modulus, dielectric constant, and contact angle, were determined. Results for specific polyimide networks are provided in TABLE 2.

Figure 9:
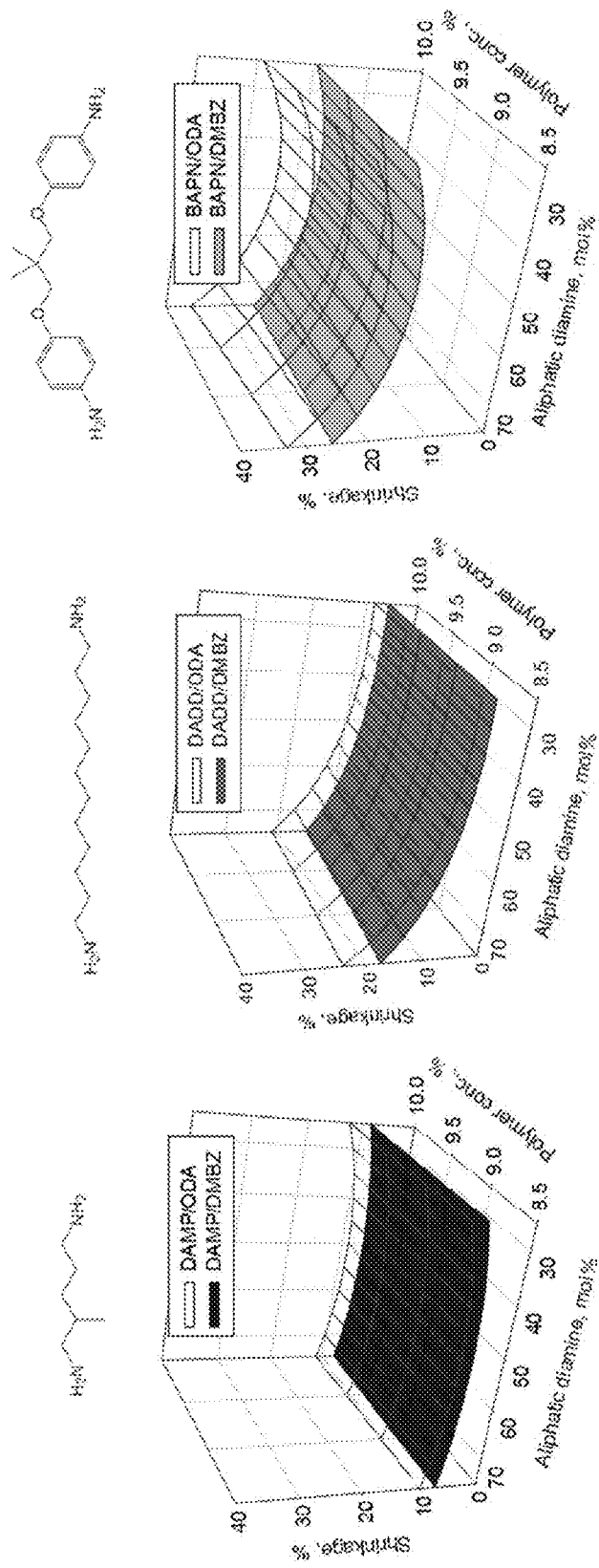
FIG. 9 shows graphs of shrinkage, % (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.063, $R^2$=0.93).

Analyses of shrinkage during processing of polyimide networks to form polyimide aerogels indicate that shrinkage during processing depends on the backbone of the polyimide network, as shown in FIG. 9. Results are provided as graphs of shrinkage, % (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.063, $R^2$=0.93). The results indicate that the polyimide networks including the diamine DMBZ typically exhibited less shrinkage than the polyimide networks including only the other diamines, reflecting a more rigid backbone and longer time to gel. Based on these results, polyimide networks including DAMP/DMBZ are predicted to shrink the least.

Figure 10:
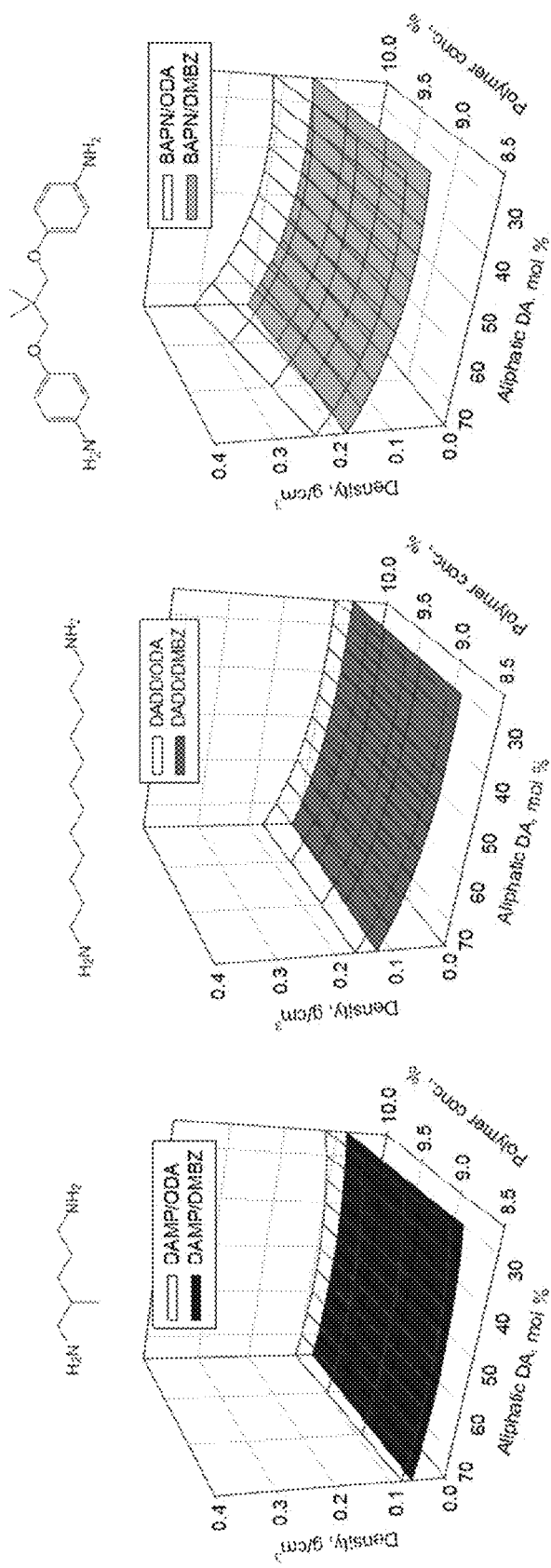
FIG. 10 shows graphs of density, $g/cm^3$ (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.037, $R^2$=0.95).

Analyses of density following processing indicate that lowest shrinkage results in lowest density, as shown in FIG. 10. Results are provided as graphs of density, $g/cm^3$ (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.037, $R^2$=0.95). Based on these results, polyimide networks including DAMP and DADD with DMBZ are predicted to result in the lowest densities.

Figure 11:
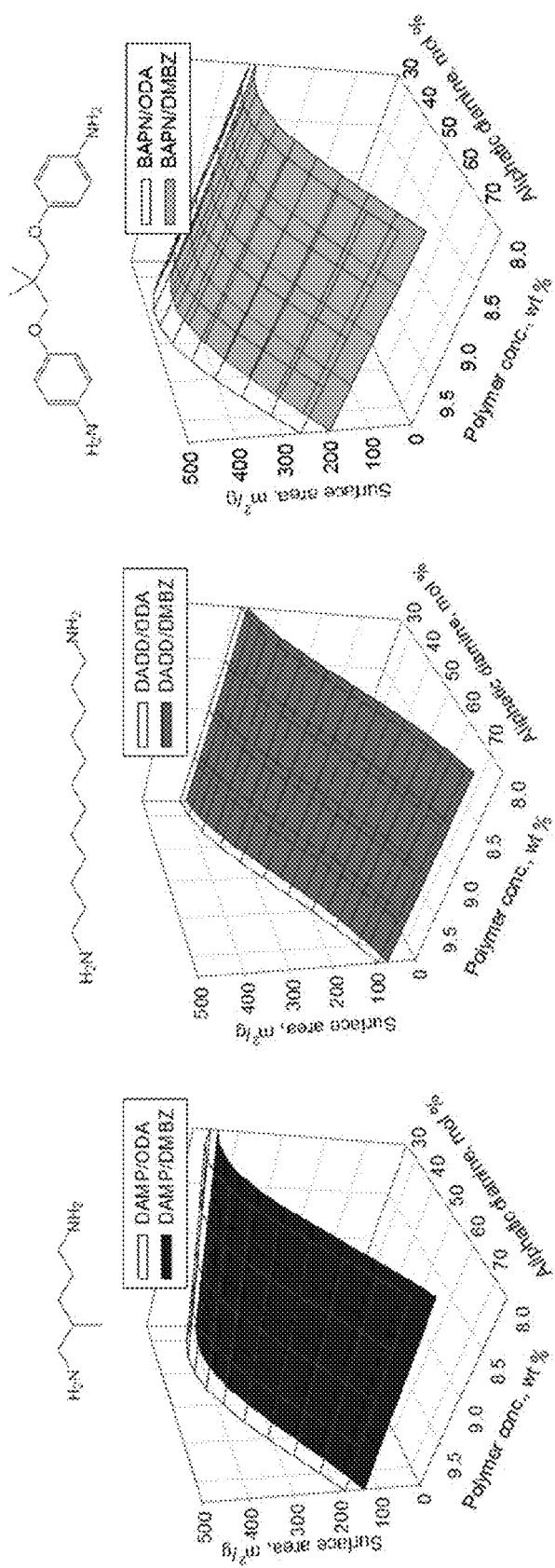
FIG. 11 shows graphs of surface area, $m^2/g$ (y-axis) as a function of polymer concentration, % (x-axis) and aliphatic diamine, mol % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.034, $R^2$=0.98).

Analyses of surface areas following processing indicate that higher concentrations of aliphatic diamines result in polyimide aerogels having lower surface areas, as shown in FIG. 11. Results are provided as graphs of surface area, $m^2/g$ (y-axis) as a function of polymer concentration, % (x-axis) and aliphatic diamine, mol % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (log SD=0.034, $R^2$=0.98). Previous observations had indicated that polyimide aerogels including DMBZ typically have higher surface areas.

Figure 12:
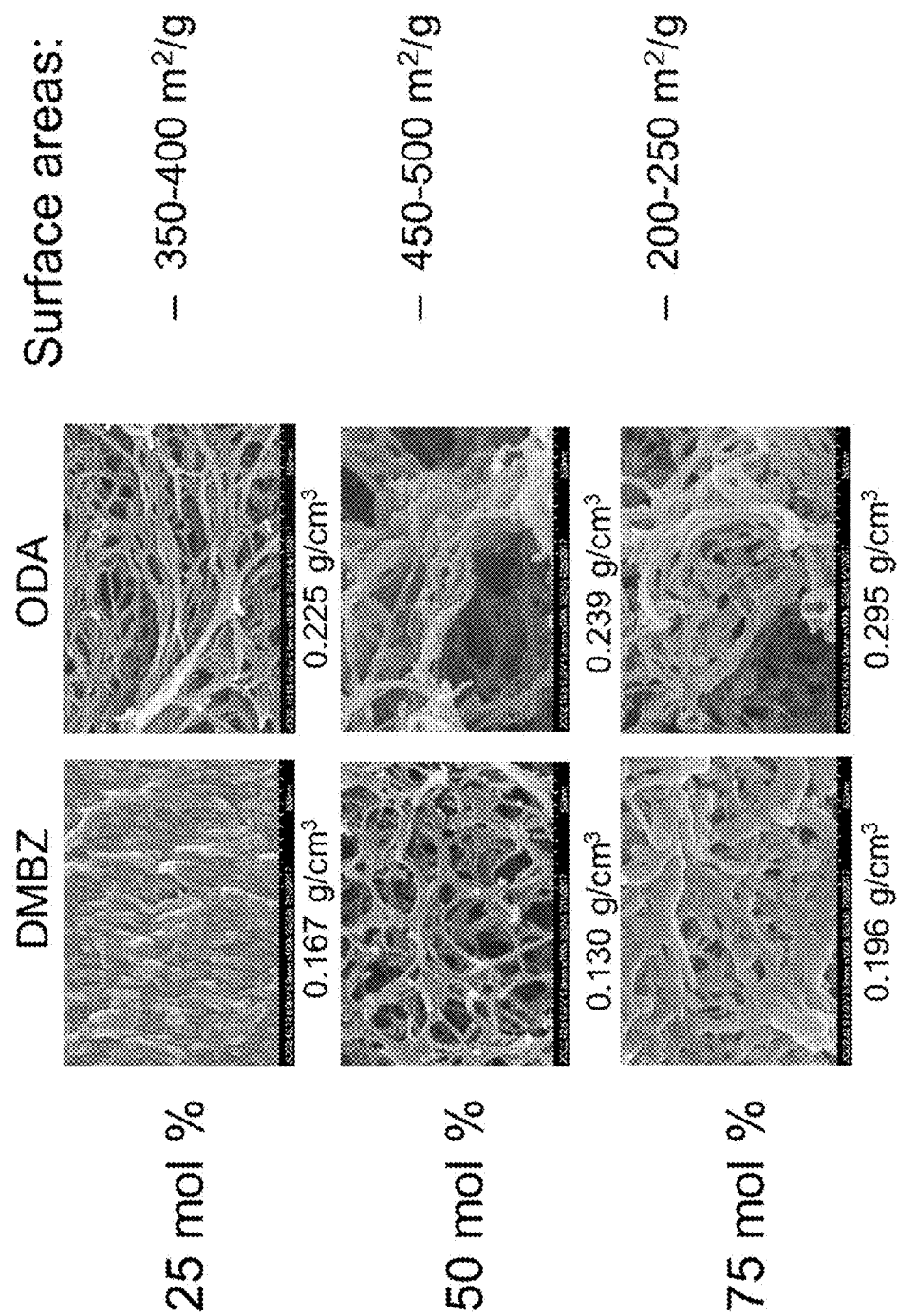
FIG. 12 shows results of scanning electron microscopy imaging of fracture surfaces of polyimide aerogels including the aliphatic diamine BAPN and either DMBZ or ODA, for which polyimide aerogel including BAPN at 25 mol % exhibited surface areas of 350 to 400 $m^2/g$, polyimide aerogel including BAPN at 50 mol % exhibited surface areas of 450 to 500 $m^2/g$, and polyimide aerogel including BAPN at 75 mol % exhibited surface areas of 200 to 250 $m^2/g$.

Results of scanning electron microscopy imaging of fracture surfaces of polyimide aerogels including the aliphatic diamine BAPN and either DMBZ or ODA are shown in FIG. 12. Variation of surface areas of the polyimide aerogels with BAPN mol % are shown. Polyimide aerogel including BAPN at 25 mol % exhibited surface areas of 350 to 400 $m^2/g$. Polyimide aerogel including BAPN at 50 mol % exhibited surface areas of 450 to 500 $m^2/g$. Polyimide aerogel including BAPN at 75 mol % exhibited surface areas of 200 to 250 $m^2/g$.

Figure 13:
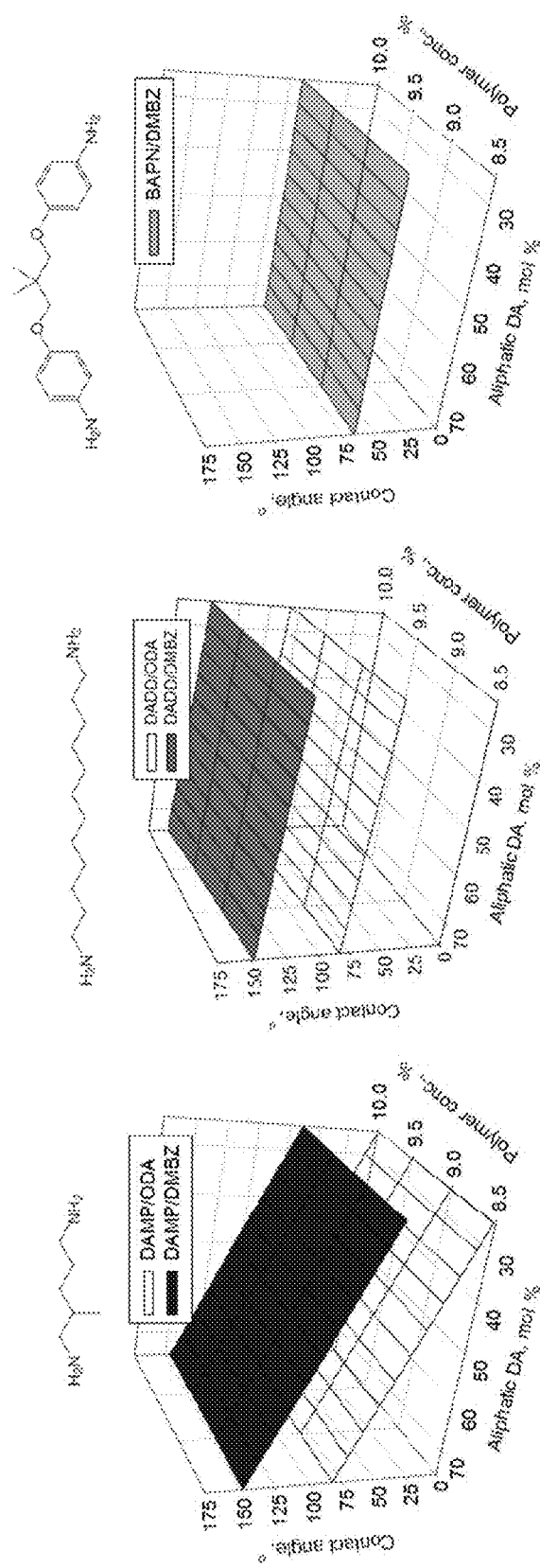
FIG. 13 shows graphs of contact angle, ° (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/DMBZ (SD=6.07, $R^2$=0.98).

Analyses of contact angles following processing indicate that the combination of DADD/DMBZ is predicted to provide the highest contact angles, as shown in FIG. 13. Results are provided as graphs of contact angle, ° (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/DMBZ (SD=6.07, $R^2$=0.98). All BAPN/ODA polyimide aerogels absorbed moisture, whereas all BAPN/DMBZ polyimide aerogels exhibited contact angles around 65°. The predictions for contact angles for polyimide aerogels including DAMP and DADD in combination with DMBZ were surprisingly high. Polyimide aerogels including 100% DMBZ as diamine exhibits a contact angle of 90°.

Analyses of dielectric constants following processing indicates that relative dielectric constants are mostly related to density of the polyimide aerogels, as shown in FIG. 14 and FIG. 15. In FIG. 14, results are provided as graphs of dielectric constant (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (SD=0.016, $R^2$=0.94). In FIG. 15, results are provided as a graph of dielectric constant, x band (y-axis) as a function of polyimide aerogel density, $g/cm^3$ (x-axis), for DMBZ/BAPN (solid black circles), ODA/BAPN (open black circles), ODA/DADD (open blue squares), and ODA/DAMP (open red circles). Dielectric constants for DMBZ with DADD and DAMP are predicted. Slight deviations were observed between samples from different studies. This may be related to how well samples fit a corresponding waveguide.

Analyses of Young's modulus following processing indicate that aliphatic diamine content appears to have only a slight effect on modulus of the polyimide aerogels, as shown in FIG. 16. This is because increasing density causes modulus to increase, and higher aliphatic diamine content increases shrinkage and therefore density is somewhat increased as previously shown. In FIG. 16, results are provided as graphs of modulus, MPa (y-axis) as a function of aliphatic diamine, mol % (x-axis) and polymer concentration, % (z-axis) for polyimide networks including dianhydride BPDA and diamines (A) DAMP/ODA or DAMP/DMBZ, (B) DADD/ODA or DADD/DMBZ, or (C) BAPN/ODA or BAPN/DMBZ (SD=0.15, $R^2$=0.68). In FIG. 17, results are provided as a graph of modulus, MPa (y-axis) as a function of polyimide aerogel density, $g/cm^3$ (x-axis), for 25% BAPN with DMBZ (open black circles), 25% BAPN with ODA (open red squares), 75% BAPN with DMBZ (solid black circles), and 75% BAPN with ODA (solid red squares). Significantly, in this plot, for example, it is shown that 75% BAPN with DMBZ does have lower modulus than 25% BAPN with DMBZ when like densities are compared. Polyimide aerogels including DMBZ in the backbone generally have higher modulus than for ODA. Modulus is affected by increase in density as content of aliphatic diamine increases.

Figure 18:
FIG. 18 demonstrates that polyimide aerogel including dianhydride BPDA and diamines BAPN at 25 mol % and DMBZ at 75 mol % is pliable in formats that are substantially thicker than thin films (e.g. 2 to 3 mm thickness or greater).

Importantly, polyimide aerogels with even only 25% aliphatic diamine are much more flexible than polyimide aerogels that do not include aliphatic diamine that have been previously tested. FIG. 18 demonstrates that polyimide aerogel including dianhydride BPDA and diamines BAPN at 25 mol % and DMBZ at 75 mol % is pliable in formats that are substantially thicker than thin films (e.g. 2 to 3 mm thickness or greater). This is in contrast to polyimide aerogels that do not include aliphatic diamine that have been previously tested, for which flexibility was limited to formats corresponding to thin films (0.5 mm thick).

The results indicate that the porous cross-linked partially aliphatic polyimide networks and polyimide aerogels exhibit increased moisture resistance and/or increased flexibility in comparison to porous cross-linked polyimide networks and polyimide aerogels that are not partially aliphatic.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

TABLE 2

Formulations and properties of porous cross-linked partially aliphatic polyimide network and polyimide aerogels.

| Run | Polymer conc., % | Aliphatic conc., % | n | Aliphatic diamine | Aromatic diamine | Density, $g/cm^3$ | Shrinkage, % | Porosity, % | Surface area, $m^2/g$ | Modulus, MPa | Dielectric constant | Contact angle, θ |
|---|---|---|---|---|---|---|---|---|---|---|---|---|
| 1 | 8.5 | 50 | 45 | BAPN | ODA | 0.2 | 29.7 | 85.7 | | 11.92 | | 0 |
| 2 | 8.5 | 50 | 45 | BAPN | ODA | 0.213 | 30.8 | 84.8 | | | | 0 |
| 3 | 8.5 | 75 | 45 | BAPN | ODA | 0.233 | 34 | 83.4 | 217 | 26.9 | | 0 |
| 4 | 8.5 | 50 | 45 | BAPN | ODA | 0.168 | 27.9 | 88.1 | | 8.52 | | 0 |

TABLE 2-continued

Formulations and properties of porous cross-linked partially aliphatic polyimide network and polyimide aerogels.

| Run | Polymer conc., % | Aliphatic conc., % | n | Aliphatic diamine | Aromatic diamine | Density, g/cm$^3$ | Shrinkage, % | Porosity, % | Surface area, m$^2$/g | Modulus, MPa | Dielectric constant | Contact angle, θ |
|---|---|---|---|---|---|---|---|---|---|---|---|---|
| 5 | 7 | 75 | 30 | BAPN | ODA | 0.192 | 28.5 | 86.6 | 197 | 22.85 | 1.21 | 0 |
| 6 | 10 | 50 | 45 | BAPN | ODA | 0.239 | 31.7 | 82.8 | | 28.96 | 1.27 | 0 |
| 7 | 8.5 | 50 | 45 | BAPN | ODA | 0.198 | 30.1 | 86.4 | | 19.97 | 1.23 | 0 |
| 8 | 10 | 75 | 60 | BAPN | ODA | 0.295 | 34 | 78.2 | | 34.34 | 1.36 | 0 |
| 9 | 7 | 75 | 60 | BAPN | ODA | 0.209 | 32.6 | 85.4 | | 11.4 | 1.22 | 0 |
| 10 | 8.5 | 25 | 45 | BAPN | ODA | | 33.8 | 82.5 | | 42.24 | 1.28 | 0 |
| 11 | 7 | 25 | 60 | BAPN | ODA | 0.156 | 27.6 | 89.2 | | 36.91 | 1.17 | 0 |
| 12 | 7 | 50 | 45 | BAPN | ODA | 0.147 | 25.1 | 89.3 | 259 | 24.32 | 1.16 | 0 |
| 13 | 10 | 75 | 30 | BAPN | ODA | 0.274 | 33.8 | 79.8 | | 51.58 | 1.3 | 0 |
| 14 | 10 | 25 | 30 | BAPN | ODA | 0.238 | 28.9 | 83.4 | | 20.95 | 1.27 | 0 |
| 15 | 8.5 | 50 | 60 | BAPN | ODA | 0.195 | 28.12 | 86.4 | | 0.47 | 1.21 | 0 |
| 16 | 8.5 | 50 | 45 | BAPN | ODA | 0.209 | 30.7 | 84.7 | | 13.56 | 1.24 | 0 |
| 17 | 8.5 | 50 | 30 | BAPN | ODA | 0.15 | 22.3 | 89.2 | | 23.46 | 1.17 | 0 |
| 18 | 10 | 25 | 60 | BAPN | ODA | 0.225 | 29.8 | 83.9 | | 27.31 | 1.26 | 0 |
| 19 | 7 | 25 | 30 | BAPN | ODA | 0.126 | 22.6 | 91.3 | 326 | 13.35 | 1.15 | 0 |
| 20 | 8.5 | 50 | 45 | BAPN | ODA | 0.198 | 28.6 | 86.2 | | | 1.22 | 0 |
| 21 | 11.5 | 75 | 30 | DAMP | ODA | 0.15 | 17.1 | 88.4 | 179 | 28.37 | 1.2 | 70.1 |
| 22 | 8.5 | 50 | 30 | DADD | ODA | 0.092 | 9 | 93 | 275 | 9.15 | 1.11 | 71.9 |
| 23 | 8.5 | 75 | 30 | DAMP | ODA | 0.08 | 10.5 | 94.1 | 191 | | 1.09 | 78.9 |
| 24 | 10 | 75 | 30 | DADD | ODA | 0.167 | 22.4 | 86.7 | 86 | 27.4 | 1.23 | 96.8 |
| 25 | 11.5 | 50 | 30 | DADD | ODA | 0.112 | 7.2 | 91.4 | 300 | 16.86 | 1.13 | 85.3 |
| 26 | 10 | 25 | 30 | DADD | ODA | 0.104 | 8.5 | 92.6 | 409 | 18.81 | 1.13 | 96.6 |
| 27 | 8.5 | 25 | 30 | DAMP | ODA | 0.1 | 10.8 | 92.6 | 454 | 11.9 | 1.13 | 0 |
| 28 | 8.5 | 25 | 30 | DAMP | ODA | 0.09 | 8.8 | 93.7 | 431 | 7.42 | 1.12 | 0 |
| 29 | 10 | 75 | 30 | DADD | ODA | 0.191 | 24.6 | 84 | | | 1.26 | 106.8 |
| 30 | 11.5 | 75 | 30 | DAMP | ODA | 0.118 | 10.8 | 91.4 | 144 | 19.51 | 1.15 | 83.5 |
| 31 | 11.5 | 25 | 30 | DAMP | ODA | 0.108 | 6.4 | 92 | 417 | | 1.13 | 99.5 |
| 32 | 11.5 | 25 | 30 | DAMP | ODA | 0.182 | 21.1 | 86.7 | 349 | 28.81 | 1.23 | 0 |
| 33 | 8.5 | 25 | 30 | DADD | ODA | 0.112 | 14.3 | 91.5 | 376 | 13.59 | 1.14 | 68.7 |
| 34 | 10 | 50 | 30 | DAMP | ODA | 0.097 | 7 | 92.8 | 362 | 15.54 | 1.12 | |
| 35 | 10 | 25 | 30 | DAMP | ODA | 0.111 | 10.3 | 92.1 | 424 | 14.95 | | 0 |
| 36 | 8.5 | 75 | 30 | DAMP | ODA | 0.083 | 9 | 93.9 | 214 | 14.98 | 1.11 | 89.7 |
| 37 | 10 | 50 | 30 | DADD | ODA | 0.107 | 9.1 | 92.1 | 300 | 12.93 | 1.2 | 73.7 |
| 38 | 8.5 | 50 | 45 | BAPN | DMBZ | 0.148 | 22.9 | 89.4 | | 41.42 | 1.18 | 79 |
| 39 | 8.5 | 50 | 45 | BAPN | DMBZ | 0.133 | 19.7 | 90.3 | | 25.62 | 1.16 | 67.6 |
| 40 | 8.5 | 75 | 45 | BAPN | DMBZ | 0.208 | 29.6 | 85.1 | | 46.45 | 1.22 | 60.4 |
| 41 | 8.5 | 50 | 45 | BAPN | DMBZ | 0.141 | 20.4 | 90.1 | | 33.08 | 1.16 | 65.2 |
| 42 | 7 | 75 | 30 | BAPN | DMBZ | 0.161 | 28.8 | 88.5 | | 15.82 | 1.19 | 56.8 |
| 43 | 10 | 50 | 45 | BAPN | DMBZ | 0.13 | 15.3 | 90.5 | | 36.1 | 1.17 | 64.4 |
| 44 | 8.5 | 50 | 45 | BAPN | DMBZ | 0.15 | 23.3 | 89.8 | | 64.69 | 1.16 | 71.1 |
| 45 | 10 | 75 | 60 | BAPN | DMBZ | 0.196 | 27.0 | 86 | 237 | 44.17 | 1.23 | 65.1 |
| 46 | 7 | 75 | 60 | BAPN | DMBZ | 0.193 | 31.1 | 86 | | 33.65 | 1.21 | 73.9 |
| 47 | 8.5 | 25 | 45 | BAPN | DMBZ | 0.143 | | 90.4 | 342 | | 1.18 | 64.0 |
| 48 | 7 | 25 | 60 | BAPN | DMBZ | 0.171 | | 88.5 | | 91.85 | 1.17 | 75.3 |
| 49 | 7 | 50 | 45 | BAPN | DMBZ | 0.126 | 22.1 | 91.1 | | 44.56 | 1.15 | 61.5 |
| 50 | 10 | 75 | 30 | BAPN | DMBZ | 0.21 | 29.1 | 84.8 | | 44.63 | 1.24 | 69.6 |
| 51 | 10 | 25 | 30 | BAPN | DMBZ | 0.15 | 18.6 | 89.3 | 388 | 34.87 | 1.18 | 64.4 |
| 52 | 8.5 | 50 | 60 | BAPN | DMBZ | 0.143 | 21.9 | 89.7 | | 30.24 | 1.16 | 60.1 |
| 53 | 8.5 | 50 | 45 | BAPN | DMBZ | 0.14 | 21.6 | 90.2 | 307 | 58.1 | 1.16 | 63.4 |
| 54 | 8.5 | 50 | 30 | BAPN | DMBZ | 0.135 | 19.6 | 90.5 | | 31.47 | 1.17 | 58.9 |
| 55 | 10 | 25 | 60 | BAPN | DMBZ | 0.167 | 22.3 | 88.1 | 459 | | 1.21 | 57.3 |
| 56 | 7 | 25 | 30 | BAPN | DMBZ | 0.109 | 19.4 | 92.1 | | 23.59 | 1.13 | 69.1 |
| 57 | 8.5 | 50 | 45 | BAPN | DMBZ | 0.137 | 21.0 | 90.2 | | 34.87 | 1.17 | 63.1 |
| 59 | 11.5 | 25 | 30 | DAMP | ODA | 0.152 | 16.8 | 90.2 | | | | |
| 66 | 10 | 75 | 30 | DAMP | ODA | 0.1075 | 11.4 | 91.3 | 192 | | | |

What is claimed is:

1. A porous cross-linked partially aliphatic polyimide network comprising a polyamic acid oligomer that (i) comprises a repeating unit of a dianhydride and a diamine and terminal functional groups, (ii) has an average degree of polymerization of 10 to 70, (iii) has been cross-linked via a cross-linking agent, comprising three or more cross-linking groups, at a balanced stoichiometry of the cross-linking groups to the terminal functional groups, and (iv) has been chemically imidized to yield the porous cross-linked polyimide network, wherein the polyimide network is partially aliphatic based on one or both of the following:

(a) the diamine comprises: (i) a first diamine at 5 to 95% (mol %) and (ii) a second diamine at 5 to 95% (mol %), wherein (1) the first diamine comprises a first diamine linear aliphatic backbone chain comprising carbon atoms and optionally one or more oxygen atoms therein, extending a length of 3 to 30 atoms, and having a ratio of carbon:oxygen of 2:1 to 3:0, and (2) the second diamine does not comprise any linear aliphatic backbone chain extending a length of 3 or more atoms; or (b) the dianhydride comprises: (i) a first dianhydride at 5 to 95% (mol %) and (ii) a second dianhydride at 5 to 95% (mol %), wherein (1) the first dianhydride comprises a first dianhydride linear aliphatic backbone chain comprising carbon atoms and optionally one or more oxygen atoms therein, extending a length of 3 to 30 atoms, and having a ratio of carbon:oxygen of 2:1 to 3:0, and (2) the second dianhydride does not comprise any linear aliphatic backbone chain extending a length of 3 or more atoms.

2. The porous cross-linked partially aliphatic polyimide network of claim 1, wherein the diamine comprises: (i) a first diamine at 5 to 95% (mol %) and (ii) a second diamine at 5 to 95% (mol %), wherein (1) the first diamine comprises a first diamine linear aliphatic backbone chain comprising carbon atoms and optionally one or more oxygen atoms therein, extending a length of 3 to 30 atoms, and having a ratio of carbon:oxygen of 2:1 to 3:0, and (2) the second diamine does not comprise any linear aliphatic backbone chain extending a length of 3 or more atoms.

3. The porous cross-linked partially aliphatic polyimide network of claim 2, wherein the first diamine comprises one or more of 1,3-bis(4-aminophenoxy)neopentane, 1,4-bis(4-aminophenoxy)butane, 1,5-bis(4-aminophenoxy)pentane, 1,6-bis(4-aminophenoxy)hexane, 1,10-bis(4-aminophenoxy)decane, 1,3-diaminopropane, 1,4-diaminobutane, 1,6-diaminohexane, 1,7-diaminoheptane, 1,9-diaminononane, 1,10-diaminodecane, 1,12-diaminododecane, 1,5-diamino-2-methylpentane, 2,2 dimethyl-1,3-propanediamine, bisaminopropyleneglycol, diaminopropylene glycol, α,ω-diaminoalkane, α,ω-bis(p-aminophenoxy)alkane, or α,ω-bis(m-aminophenoxy)alkane.

4. The porous cross-linked partially aliphatic polyimide network of claim 2, wherein the second diamine comprises one or more of 2,2'-dimethylbenzidine, 2,2'-bis[4-(4-aminophenoxy)phenyl]propane, 4,4'-diaminobenzophenone, 4,4'-oxydianiline, 3,4'-oxydianiline, p-phenylene diamine, bisaniline-p-xylidene, 4,4'-bis(4-aminophenoxy)biphenyl, 3,3'-bis(4-aminophenoxy)biphenyl, 4,4'-(1,4-phenylenediisopropylidene)bisaniline, 4,4'-(1,3-phenylenediisopropylidene)bisaniline, 4,4' (hexafluoroisopropylidene)dianiline, 4,4'-(hexafluoroisopropylidene)bis(p-phenylenoxy)dianiline, or 2,2'-bis(trifluoromethyl)benzidine.

5. The porous cross-linked partially aliphatic polyimide network of claim 2, wherein the dianhydride comprises one or more of biphenyl-3,3',4,4'-tetracarboxylic dianhydride, benzophenone-3,3',4,4'-tetracarboxylic dianhydride, pyromellitic dianhydride, 4,4'-oxydiphthalic anhydride, or 2,2'-bis(3,4'-dicarboxyphenyl)hexafluoropropane dianhydride.

6. The porous cross-linked partially aliphatic polyimide network of claim 2, wherein the first diamine linear aliphatic backbone chain comprises at least one of an alkyl chain, an unsubstituted alkyl chain, a substituted alkyl chain, an alkyl alkyl ether chain, an unsubstituted alkyl alkyl ether chain, or a substituted alkyl alkyl ether chain.

7. The porous cross-linked partially aliphatic polyimide network of claim 1, wherein the dianhydride comprises: (i) a first dianhydride at 5 to 95% (mol %) and (ii) a second dianhydride at 5 to 95% (mol %), wherein (1) the first dianhydride comprises a first dianhydride linear aliphatic backbone chain comprising carbon atoms and optionally one or more oxygen atoms therein, extending a length of 3 to 30 atoms, and having a ratio of carbon:oxygen of 2:1 to 3:0, and (2) the second dianhydride does not comprise any linear aliphatic backbone chain extending a length of 3 or more atoms.

8. The porous cross-linked partially aliphatic polyimide network of claim 7, wherein the first dianhydride comprises one or more of [α,ω-alkanediylbis(oxy)]bis-1,3-isobenzofurandione or bis-α,ω-[isobenzofurandione]alkane.

9. The porous cross-linked partially aliphatic polyimide network of claim 7, wherein the second dianhydride comprises one or more of biphenyl-3,3',4,4'-tetracarboxylic dianhydride, benzophenone-3,3',4,4'-tetracarboxylic dianhydride, pyromellitic dianhydride, 4,4'-oxydiphthalic anhydride, or 2,2'-bis(3,4'-dicarboxyphenyl)hexafluoropropane dianhydride.

10. The porous cross-linked partially aliphatic polyimide network of claim 7, wherein the diamine comprises one or more of 2,2'-dimethylbenzidine, 2,2'-bis[4-(4-aminophenoxy)phenyl]propane, 4,4'-diaminobenzophenone, 4,4'-oxydianiline, 3,4'-oxydianiline, p-phenylene diamine, bisaniline-p-xylidene, 4,4'-bis(4-aminophenoxy)biphenyl, 3,3'-bis(4-aminophenoxy)biphenyl, 4,4'-(1,4-phenylenediisopropylidene)bisaniline, 4,4'-(1,3-phenylenediisopropylidene)bisaniline, 4,4' (hexafluoroisopropylidene)dianiline, 4,4'-(hexafluoroisopropylidene)bis(p-phenylenoxy)dianiline, or 2,2'-bis(trifluoromethyl)benzidine.

11. The porous cross-linked partially aliphatic polyimide network of claim 7, wherein the first dianhydride linear aliphatic backbone chain comprises at least one of an alkyl chain, an unsubstituted alkyl chain, a substituted alkyl chain, an alkyl alkyl ether chain, an unsubstituted alkyl alkyl ether chain, or a substituted alkyl alkyl ether chain.

12. The porous cross-linked partially aliphatic polyimide network of claim 1, wherein the terminal functional groups comprise (i) terminal anhydride groups, such that the polyamic acid oligomer comprises an anhydride end-capped polyamic acid oligomer, or (ii) terminal amine groups, such that the polyamic acid oligomer comprises an amine end-capped polyamic acid oligomer.

13. The porous cross-linked partially aliphatic polyimide network of claim 1, wherein the three or more cross-linking groups comprise one or more of isocyanate groups, amine groups, anhydride groups, or acid chloride groups.

14. The porous cross-linked partially aliphatic polyimide network of claim 13, wherein the three or more cross-linking groups comprise isocyanate groups, and the cross-linking agent comprises one or more of a triisocyanate, trifunctional aliphatic isocyanate Desmodur N3300A, or aliphatic polyisocyanate Desmodur Z4470.

15. The porous cross-linked partially aliphatic polyimide network of claim 13, wherein the three or more cross-linking groups comprise amine groups, and the cross-linking agent comprises one or more of a triamine, an aliphatic amine comprising three or more amines, an aliphatic triamine, an aromatic amine comprising three or more amine groups, an aromatic triamine, 1,3,5-tri(aminophenoxy)benzene, a silica cage structure decorated with three or more amines, octa(aminophenyl)silsesquioxane, octa(aminophenyl)silsesquioxane as a mixture of isomers having the ratio meta:ortho:para of 60:30:10, or para-octa(aminophenyl)silsesquioxane.

16. The porous cross-linked partially aliphatic polyimide network of claim 13, wherein the three or more cross-linking groups comprise anhydride groups, and the cross-linking agent comprises polymaleic anhydride.

17. The porous cross-linked partially aliphatic polyimide network of claim 13, wherein the three or more cross-linking groups comprise acid chloride groups, and the cross-linking agent comprises one or more of a triacid chloride or 1,3,5-benzenetricarbonyl trichloride.

18. The porous cross-linked partially aliphatic polyimide network of claim 1, wherein the polyamic acid oligomer has been chemically imidized to completion.

19. An aerogel comprising the porous cross-linked partially aliphatic polyimide network of claim 1.

20. The aerogel of claim 19, wherein the aerogel has a density of 0.080 to 0.30 g/cm$^3$.

21. The aerogel of claim 19, wherein the aerogel has a surface area of 200 to 500 m$^2$/g.

22. The aerogel of claim 19, wherein the aerogel has a water contact angle of 60 to 150°.

23. The aerogel of claim 19, wherein the aerogel has a dielectric constant of 1.08 to 1.36.

24. The aerogel of claim 19, wherein the aerogel has a Young's modulus of 10 to 100 MPa.

25. The aerogel of claim 19, wherein the aerogel maintains flexibility at a thickness of 2 to 3 mm.

* * * * *